(12) United States Patent
Pierce et al.

(10) Patent No.: US 8,302,607 B2
(45) Date of Patent: *Nov. 6, 2012

(54) ADHESIVE NASAL RESPIRATORY DEVICES

(75) Inventors: Ryan Kendall Pierce, San Francisco, CA (US); Bryan Loomas, Los Gatos, CA (US); Rajiv Doshi, Los Altos, CA (US); Jonathan P. Summers, Redwood City, CA (US); Jeffrey W. Servaites, San Francisco, CA (US); Arthur Ferdinand, San Jose, CA (US); Arthur G. Sandoval, San Francisco, CA (US); Toru Mino, Chicago, IL (US)

(73) Assignee: Ventus Medical, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/299,181

(22) Filed: Nov. 17, 2011

(65) Prior Publication Data

US 2012/0055488 A1 Mar. 8, 2012

Related U.S. Application Data

(63) Continuation of application No. 12/141,875, filed on Jun. 18, 2008, now Pat. No. 8,061,357, which is a continuation-in-part of application No. 11/298,339, filed on Dec. 8, 2005, now Pat. No. 7,798,148, and a continuation-in-part of application No. 11/759,916, filed on Jun. 7, 2007.

(60) Provisional application No. 60/634,715, filed on Dec. 8, 2004, provisional application No. 61/037,180, filed on Mar. 17, 2008.

(51) Int. Cl.
*A61M 16/00* (2006.01)
*A62B 7/00* (2006.01)

(52) U.S. Cl. ................................ 128/207.18; 128/848
(58) Field of Classification Search ............. 128/200.24, 128/205.27, 205.29, 206.11, 207.18
See application file for complete search history.

(56) References Cited

U.S. PATENT DOCUMENTS

| 69,396 | A | 10/1867 | Curtis |
| 628,111 | A | 7/1899 | McHatton |
| 669,098 | A | 3/1901 | Overshiner |
| 675,275 | A | 5/1901 | Gunning |
| 718,785 | A | 1/1903 | McNary |

(Continued)

FOREIGN PATENT DOCUMENTS

EP 0434258 A2 6/1991

(Continued)

OTHER PUBLICATIONS http://chinookmed.com/index.cfm/fa/product.display&Product_ID=275; accessed Nov. 28, 2007.

(Continued)

*Primary Examiner* — Patricia Bianco
*Assistant Examiner* — Tarla Patel
(74) *Attorney, Agent, or Firm* — Shay Glenn LLP

(57) ABSTRACT

Whole-nose nasal respiratory devices and methods of making and using whole-nose nasal respiratory devices are described and illustrated herein. These devices are typically configured to be adhesively secured to a subject so that they engage both of the subject's nostrils and allow airflow from both nostrils to communicate with an airflow resistor. The airflow resistor is configured so that it inhibits exhalation through the nostrils more than it inhibits inhalation through the nostrils.

12 Claims, 30 Drawing Sheets

U.S. PATENT DOCUMENTS

| | | |
|---|---|---|
| 746,869 A | 12/1903 | Moulton |
| 774,446 A | 11/1904 | Moulton |
| 810,617 A | 1/1906 | Carence |
| 1,819,884 A | 8/1931 | Fores |
| 2,198,959 A | 4/1940 | Clarke |
| 2,237,954 A | 4/1941 | Wilson |
| 2,264,153 A | 11/1941 | Rowe |
| 2,274,886 A | 3/1942 | Carroll |
| 2,282,681 A | 5/1942 | Stotz |
| 2,335,936 A | 12/1943 | Hanlon |
| 2,433,565 A | 12/1947 | Korman |
| 2,448,724 A | 9/1948 | McGovney |
| 2,593,315 A | 4/1952 | Kraft |
| 2,672,138 A | 3/1954 | Garlock |
| 2,751,906 A | 6/1956 | Irvine |
| 2,777,442 A | 1/1957 | Zelano |
| 3,145,711 A | 8/1964 | Beber |
| 3,370,305 A | 2/1968 | Goott et al. |
| 3,451,392 A | 6/1969 | Cook et al. |
| 3,463,149 A | 8/1969 | Albu |
| 3,513,839 A | 5/1970 | Vacante |
| 3,556,122 A | 1/1971 | Laerdal |
| 3,616,802 A | 11/1971 | Marinaccio |
| 3,657,855 A | 4/1972 | Swezey |
| 3,695,265 A | 10/1972 | Brevik |
| 3,710,799 A | 1/1973 | Caballero |
| 3,722,509 A | 3/1973 | Nebel |
| 3,747,597 A | 7/1973 | Olivera |
| 3,802,426 A | 4/1974 | Sakamoto |
| 3,884,223 A | 5/1975 | Keindl |
| 3,902,621 A | 9/1975 | Hidding |
| 4,004,584 A | 1/1977 | Geaney |
| 4,030,491 A | 6/1977 | Mattila |
| 4,040,428 A | 8/1977 | Clifford |
| 4,054,134 A | 10/1977 | Kritzer |
| 4,062,358 A | 12/1977 | Kritzer |
| 4,094,316 A | 6/1978 | Nathanson |
| 4,143,872 A | 3/1979 | Havstad et al. |
| 4,212,296 A | 7/1980 | Schaar |
| 4,220,150 A | 9/1980 | King |
| 4,221,217 A | 9/1980 | Amezcua |
| 4,226,233 A | 10/1980 | Kritzer |
| 4,240,420 A | 12/1980 | Riaboy |
| 4,267,831 A | 5/1981 | Aguilar |
| 4,327,719 A | 5/1982 | Childers |
| RE31,040 E | 9/1982 | Possis |
| 4,354,489 A | 10/1982 | Riaboy |
| 4,403,616 A | 9/1983 | King |
| 4,456,016 A | 6/1984 | Nowacki et al. |
| 4,487,207 A | 12/1984 | Fitz |
| 4,533,137 A | 8/1985 | Sonne |
| 4,582,058 A | 4/1986 | Depel et al. |
| 4,601,465 A | 7/1986 | Roy |
| 4,640,277 A | 2/1987 | Meyer et al. |
| 4,651,873 A | 3/1987 | Stolcenberg et al. |
| 4,702,374 A | 10/1987 | Kelner |
| 4,718,554 A | 1/1988 | Barbato |
| 4,739,987 A | 4/1988 | Nicholson |
| 4,822,354 A | 4/1989 | Elosegui |
| 4,854,574 A | 8/1989 | Larson et al. |
| 4,860,766 A | 8/1989 | Sackner |
| 4,862,903 A | 9/1989 | Campbell |
| 4,908,028 A | 3/1990 | Colon et al. |
| 4,913,138 A | 4/1990 | Yoshida et al. |
| 4,919,138 A | 4/1990 | Nordenstroom |
| 4,973,047 A | 11/1990 | Norell |
| 4,979,505 A | 12/1990 | Cox |
| 4,984,302 A | 1/1991 | Lincoln |
| 4,984,581 A | 1/1991 | Stice |
| 5,016,425 A | 5/1991 | Weick |
| 5,033,312 A | 7/1991 | Stupecky |
| 5,038,621 A | 8/1991 | Stupecky |
| 5,059,208 A | 10/1991 | Coe et al. |
| 5,074,293 A | 12/1991 | Lott et al. |
| 5,078,739 A | 1/1992 | Martin |
| 5,092,781 A | 3/1992 | Casciotti et al. |
| 5,117,820 A | 6/1992 | Robitaille |
| 5,197,980 A | 3/1993 | Gorshkov et al. |
| 5,255,687 A | 10/1993 | McKenna |
| 5,383,470 A | 1/1995 | Kolbly |
| 5,385,542 A | 1/1995 | Rawlings |
| 5,391,205 A | 2/1995 | Knight |
| 5,392,773 A | 2/1995 | Bertrand |
| 5,394,867 A | 3/1995 | Swann |
| 5,414,627 A | 5/1995 | Wada et al. |
| 5,415,660 A | 5/1995 | Campbell et al. |
| 5,425,359 A | 6/1995 | Liou |
| 5,459,544 A | 10/1995 | Emura |
| 5,522,382 A | 6/1996 | Sullivan et al. |
| 5,535,739 A | 7/1996 | Rapoport et al. |
| 5,562,641 A | 10/1996 | Flomenblit et al. |
| 5,568,808 A | 10/1996 | Rimkus |
| 5,607,469 A | 3/1997 | Frey |
| 5,649,533 A | 7/1997 | Oren |
| 5,665,104 A | 9/1997 | Lee |
| 5,727,546 A | 3/1998 | Clarke et al. |
| 5,740,798 A | 4/1998 | McKinney |
| 5,743,256 A | 4/1998 | Jalowayski |
| 5,763,979 A | 6/1998 | Mukherjee et al. |
| 5,775,335 A | 7/1998 | Seal |
| 5,782,896 A | 7/1998 | Chen et al. |
| 5,797,920 A | 8/1998 | Kim |
| 5,803,121 A | 9/1998 | Estes |
| 5,823,187 A | 10/1998 | Estes et al. |
| 5,865,170 A | 2/1999 | Moles |
| 5,876,434 A | 3/1999 | Flomenblit et al. |
| 5,890,998 A | 4/1999 | Hougen |
| 5,899,832 A | 5/1999 | Hougen |
| 5,910,071 A | 6/1999 | Hougen |
| 5,911,756 A | 6/1999 | Debry |
| 5,947,119 A | 9/1999 | Reznick |
| 5,954,766 A | 9/1999 | Zadno-Azizi et al. |
| 5,957,978 A | 9/1999 | Blom |
| 5,992,006 A | 11/1999 | Datsikas |
| 6,004,342 A | 12/1999 | Filis |
| 6,058,932 A | 5/2000 | Hughes |
| 6,083,141 A | 7/2000 | Hougen |
| D430,667 S | 9/2000 | Rome |
| 6,119,690 A | 9/2000 | Pantaleo |
| 6,165,133 A | 12/2000 | Rapoport et al. |
| 6,177,482 B1 | 1/2001 | Cinelli et al. |
| 6,189,532 B1 | 2/2001 | Hely et al. |
| 6,213,955 B1 | 4/2001 | Karakasoglu et al. |
| 6,219,997 B1 | 4/2001 | Friberg et al. |
| 6,258,100 B1 | 7/2001 | Alferness et al. |
| 6,287,290 B1 | 9/2001 | Perkins et al. |
| 6,293,951 B1 | 9/2001 | Alferness et al. |
| 6,311,839 B1 | 11/2001 | Lo |
| 6,369,126 B1 | 4/2002 | Cinelli et al. |
| 6,398,775 B1 | 6/2002 | Perkins et al. |
| 6,439,233 B1 | 8/2002 | Geertsema |
| 6,484,725 B1 | 11/2002 | Chi |
| 6,500,095 B1 | 12/2002 | Hougen |
| 6,510,846 B1 | 1/2003 | O'Rourke |
| 6,527,761 B1 | 3/2003 | Soltesz et al. |
| 6,561,188 B1 | 5/2003 | Ellis |
| 6,562,057 B2 | 5/2003 | Santin |
| 6,568,387 B2 | 5/2003 | Davenport et al. |
| 6,573,421 B1 | 6/2003 | Lemaire |
| 6,581,598 B1 | 6/2003 | Foran et al. |
| 6,585,639 B1 | 7/2003 | Kotmel et al. |
| 6,592,594 B2 | 7/2003 | Rimbaugh et al. |
| 6,592,995 B2 | 7/2003 | Topolkaraev et al. |
| 6,595,215 B2 | 7/2003 | Wood |
| 6,609,516 B2 | 8/2003 | Hollander et al. |
| 6,626,172 B1 | 9/2003 | Karow et al. |
| 6,626,179 B1 | 9/2003 | Pedley |
| 6,631,721 B1 | 10/2003 | Salter et al. |
| 6,679,264 B1 | 1/2004 | Deem et al. |
| 6,694,979 B2 | 2/2004 | Deem et al. |
| 6,722,360 B2 | 4/2004 | Doshi |
| 6,726,598 B1 | 4/2004 | Jarvis et al. |
| 6,737,160 B1 | 5/2004 | Full et al. |
| 6,769,432 B1 | 8/2004 | Keifer |
| 6,776,162 B2 | 8/2004 | Wood |
| 6,811,538 B2 | 11/2004 | Westbrook et al. |
| 6,841,716 B1 | 1/2005 | Tsutsumi |

| Patent No. | Date | Inventor |
|---|---|---|
| 6,848,446 B2 | 2/2005 | Noble |
| 6,863,066 B2 | 3/2005 | Ogle |
| 6,866,652 B2 | 3/2005 | Bierman |
| 6,872,439 B2 | 3/2005 | Fearing et al. |
| 6,921,574 B2 | 7/2005 | Cinelli et al. |
| 6,997,177 B2 | 2/2006 | Wood |
| 7,011,723 B2 | 3/2006 | Full et al. |
| 7,047,969 B2 | 5/2006 | Noble |
| 7,156,098 B2 | 1/2007 | Dolezal et al. |
| 7,175,723 B2 | 2/2007 | Jones et al. |
| 7,178,524 B2 | 2/2007 | Noble |
| 7,201,169 B2 | 4/2007 | Wilkie et al. |
| D542,407 S | 5/2007 | Stallard et al. |
| 7,263,996 B2 | 9/2007 | Yung Ho |
| 7,334,581 B2 | 2/2008 | Doshi |
| D566,834 S | 4/2008 | Barton |
| 7,422,014 B1 | 9/2008 | Smith |
| 7,506,649 B2 | 3/2009 | Doshi et al. |
| 7,559,326 B2 | 7/2009 | Smith et al. |
| 7,640,934 B2 | 1/2010 | Zollinger et al. |
| 7,735,491 B2 | 6/2010 | Doshi et al. |
| 7,735,492 B2 | 6/2010 | Doshi et al. |
| 7,798,148 B2 | 9/2010 | Doshi et al. |
| 7,806,120 B2 | 10/2010 | Loomas et al. |
| 7,856,979 B2 | 12/2010 | Doshi et al. |
| 7,880,051 B2 | 2/2011 | Madsen et al. |
| 7,987,852 B2 | 8/2011 | Doshi et al. |
| 7,992,563 B2 | 8/2011 | Doshi |
| 7,992,564 B2 | 8/2011 | Doshi et al. |
| 8,020,700 B2 | 9/2011 | Doshi et al. |
| 8,061,357 B2 | 11/2011 | Pierce et al. |
| 2001/0051799 A1 | 12/2001 | Ingenito |
| 2001/0056274 A1 | 12/2001 | Perkins et al. |
| 2002/0062120 A1 | 5/2002 | Perkins et al. |
| 2002/0077593 A1 | 6/2002 | Perkins et al. |
| 2002/0112729 A1 | 8/2002 | DeVore et al. |
| 2002/0157673 A1 | 10/2002 | Kessler et al. |
| 2003/0024527 A1 | 2/2003 | Ginn |
| 2003/0050648 A1 | 3/2003 | Alferness et al. |
| 2003/0070682 A1 | 4/2003 | Wilson et al. |
| 2003/0106555 A1 | 6/2003 | Tovey |
| 2003/0106556 A1 | 6/2003 | Alperovich et al. |
| 2003/0140925 A1 | 7/2003 | Sapienza et al. |
| 2003/0149387 A1 | 8/2003 | Barakat et al. |
| 2003/0154988 A1 | 8/2003 | DeVore et al. |
| 2003/0158515 A1 | 8/2003 | Gonzalez et al. |
| 2003/0195552 A1 | 10/2003 | Santin |
| 2003/0209247 A1 | 11/2003 | O'Rourke |
| 2004/0016432 A1 | 1/2004 | Genger et al. |
| 2004/0020492 A1 | 2/2004 | Dubrul et al. |
| 2004/0020493 A1 | 2/2004 | Wood |
| 2004/0055606 A1 | 3/2004 | Hendricksen et al. |
| 2004/0112379 A1 | 6/2004 | Djupesland |
| 2004/0123868 A1 | 7/2004 | Rutter |
| 2004/0149615 A1 | 8/2004 | Eisenbraun |
| 2004/0254491 A1 | 12/2004 | Ricciardelli |
| 2004/0261791 A1 | 12/2004 | Horian |
| 2004/0261798 A1 | 12/2004 | Rimkus |
| 2005/0010125 A1 | 1/2005 | Joy et al. |
| 2005/0011524 A1 | 1/2005 | Thomlinson et al. |
| 2005/0033344 A1 | 2/2005 | Dillard et al. |
| 2005/0051170 A1 | 3/2005 | Koo |
| 2005/0066965 A1 | 3/2005 | Cronk et al. |
| 2005/0133039 A1 | 6/2005 | Wood |
| 2005/0279351 A1 | 12/2005 | Lewis et al. |
| 2005/0284479 A1 | 12/2005 | Schrader et al. |
| 2006/0000472 A1 | 1/2006 | Fenton |
| 2006/0016450 A1 | 1/2006 | Pearson et al. |
| 2006/0085027 A1 | 4/2006 | Santin et al. |
| 2006/0169285 A1 | 8/2006 | Bovo |
| 2006/0180149 A1 | 8/2006 | Matarasso |
| 2006/0266361 A1 | 11/2006 | Hernandez |
| 2006/0283461 A1 | 12/2006 | Lubke et al. |
| 2007/0016123 A1 | 1/2007 | Jensen |
| 2007/0051364 A1 | 3/2007 | Jacobson et al. |
| 2007/0095349 A1 | 5/2007 | Hansmann et al. |
| 2007/0175478 A1 | 8/2007 | Brunst |
| 2007/0227542 A1 | 10/2007 | Kashmakov et al. |
| 2007/0283962 A1 | 12/2007 | Doshi et al. |
| 2007/0287976 A1 | 12/2007 | Sherrill |
| 2008/0023007 A1 | 1/2008 | Dolezal et al. |
| 2008/0032119 A1 | 2/2008 | Feldhahn et al. |
| 2008/0041397 A1 | 2/2008 | Hirs |
| 2008/0053460 A1 | 3/2008 | Wilson |
| 2008/0087286 A1 | 4/2008 | Jones |
| 2008/0099021 A1 | 5/2008 | Moore |
| 2008/0142014 A1 | 6/2008 | Jiang |
| 2008/0142018 A1 | 6/2008 | Doshi et al. |
| 2008/0178874 A1 | 7/2008 | Doshi et al. |
| 2008/0221470 A1 | 9/2008 | Sather et al. |
| 2009/0145441 A1 | 6/2009 | Doshi et al. |
| 2009/0194100 A1 | 8/2009 | Minagi |
| 2009/0194109 A1 | 8/2009 | Doshi et al. |
| 2009/0241965 A1 | 10/2009 | Sather et al. |
| 2009/0308398 A1 | 12/2009 | Ferdinand et al. |
| 2010/0326447 A1 | 12/2010 | Loomas et al. |
| 2011/0005520 A1 | 1/2011 | Doshi et al. |
| 2011/0005528 A1 | 1/2011 | Doshi et al. |
| 2011/0005529 A1 | 1/2011 | Doshi et al. |
| 2011/0005530 A1 | 1/2011 | Doshi et al. |
| 2011/0056499 A1 | 3/2011 | Doshi et al. |
| 2011/0067708 A1 | 3/2011 | Doshi et al. |
| 2011/0067709 A1 | 3/2011 | Doshi et al. |
| 2011/0108041 A1 | 5/2011 | Sather et al. |
| 2011/0203598 A1 | 8/2011 | Favet et al. |
| 2011/0218451 A1 | 9/2011 | Lai et al. |
| 2011/0240032 A1 | 10/2011 | Doshi |
| 2011/0240038 A1 | 10/2011 | Doshi et al. |
| 2011/0290256 A1 | 12/2011 | Sather et al. |
| 2012/0031048 A1 | 2/2012 | Doshi et al. |

FOREIGN PATENT DOCUMENTS

| | | |
|---|---|---|
| EP | 1157663 A1 | 11/2001 |
| EP | 1205203 A2 | 5/2002 |
| EP | 1481702 A2 | 12/2004 |
| FR | 2862614 A1 | 5/2005 |
| GB | 2096574 A | 10/1982 |
| GB | 2324729 A | 4/1998 |
| JP | 52-123786 A | 10/1977 |
| JP | 55-122742 U | 9/1980 |
| JP | 58-136345 A | 8/1983 |
| JP | 63-189257 U | 12/1988 |
| JP | 7-47126 | 2/1995 |
| JP | 3059270 U | 3/1999 |
| JP | 2001-299916 A | 10/2001 |
| JP | 2002-153489 A | 5/2002 |
| JP | 2002-219174 A | 8/2002 |
| JP | 2002-345963 A | 12/2002 |
| JP | 2002-345966 | 12/2002 |
| JP | 05/40589 A | 2/2005 |
| JP | 2005-505355 | 2/2005 |
| JP | 2008-136496 | 6/2008 |
| JP | 2008-522763 | 7/2008 |
| RU | 2048820 C1 | 11/1995 |
| SU | 1586709 A1 | 8/1990 |
| WO | WO 90/12614 A1 | 11/1990 |
| WO | WO 93/08777 A1 | 5/1993 |
| WO | WO 95/17220 A1 | 6/1995 |
| WO | WO 95/33520 A1 | 12/1995 |
| WO | WO 99/03395 A1 | 1/1999 |
| WO | WO 00/29066 A1 | 5/2000 |
| WO | WO 00/50121 A1 | 8/2000 |
| WO | WO 00/67848 A1 | 11/2000 |
| WO | WO 01/02042 A1 | 1/2001 |
| WO | WO 01/13839 A1 | 3/2001 |
| WO | WO 01/13908 A2 | 3/2001 |
| WO | WO 01/49371 A2 | 7/2001 |
| WO | WO 01/62342 A1 | 8/2001 |
| WO | WO 01/87170 A1 | 11/2001 |
| WO | WO 01/89381 A1 | 11/2001 |
| WO | WO 02/38038 A2 | 5/2002 |
| WO | WO 03/022124 A2 | 3/2003 |
| WO | WO 03/034927 A1 | 5/2003 |
| WO | WO 2004/084998 A1 | 10/2004 |
| WO | WO 2005/000805 A2 | 1/2005 |
| WO | WO 2006/040585 A1 | 4/2006 |
| WO | WO 2007/023607 | 3/2007 |

| WO | WO 2007/129814 A1 | 11/2007 |
| WO | WO 2007/134458 A1 | 11/2007 |
| WO | WO 2007/146133 A2 | 12/2007 |

OTHER PUBLICATIONS

Mahadevia, A. K. et al., Effects of expiratory positive airway pressure on sleep-induced respiratory abnormalities in patients with hypersomnia-sleep apnea syndrome, Am Rev Respir Dis 1983, vol. 128, pp. 708-711, Oct. 1983.

Dillard, D. et al., Evaluation of a novel intra-bronchial valve to produce lung volume reduction, World Congress of Bronchology, Jun. 2002 (figs. 1-4 available upon request).

Hakel et al.; Nasal obturator for velopharyngeal dysfunction in dysarthria: technical report on a one-way valve; Journal of Medical Speech-Language Pathology; vol. 12; No. 4; pp. 155-159; Dec. 2004.

Suwaki et al.; Nasal speaking valve: a device for managing velopharyngeal incompetence; Journal of Oral Rehabilitation; vol. 35(1); pp. 73-78; Jan. 2008.

Suwaki et al.; The effect of nasal speaking valve on the speech under experimental velopharyngeal incompetence condition; Journal of Oral Rehabilitation; vol. 35(5); pp. 361-369; May 2008.

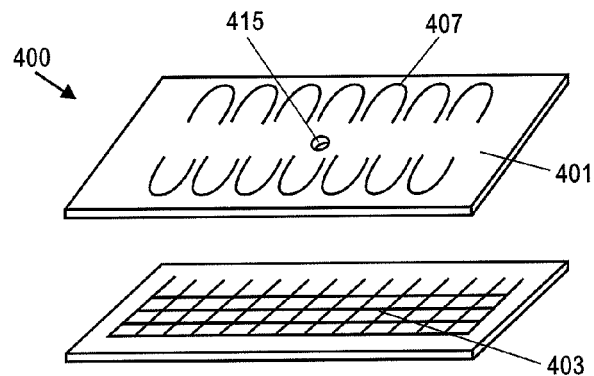
FIG. 4A
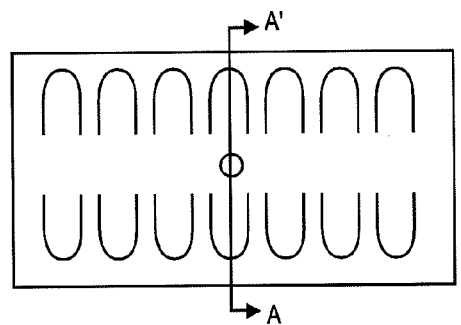
FIG. 4B
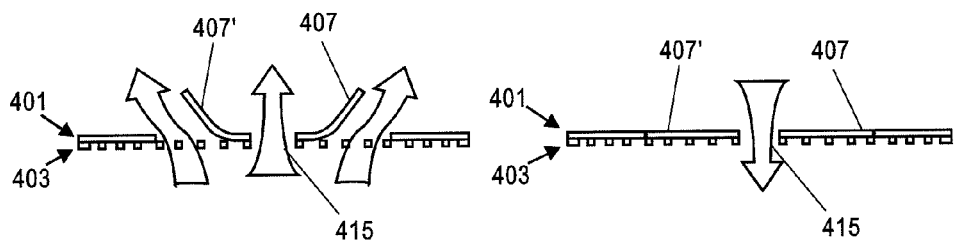
FIG. 4C  FIG. 4D

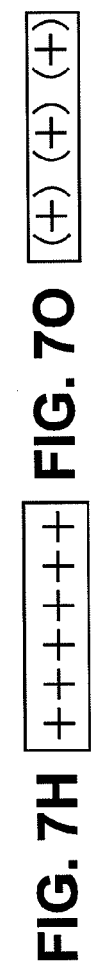
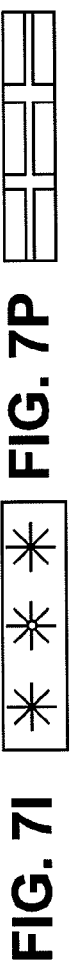
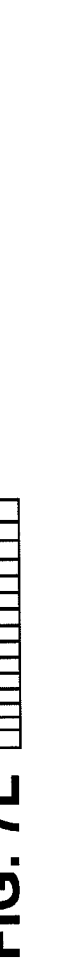

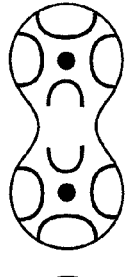
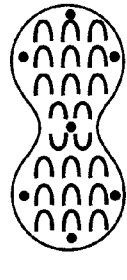
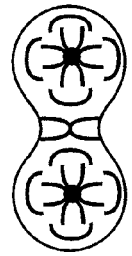
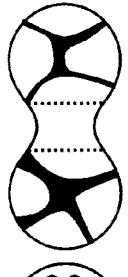
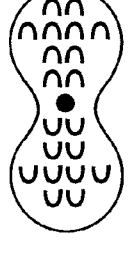
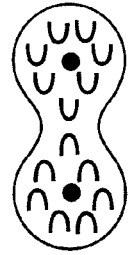
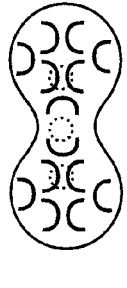
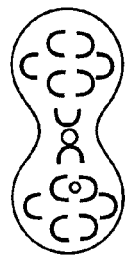
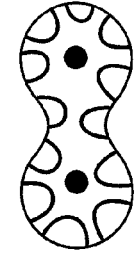

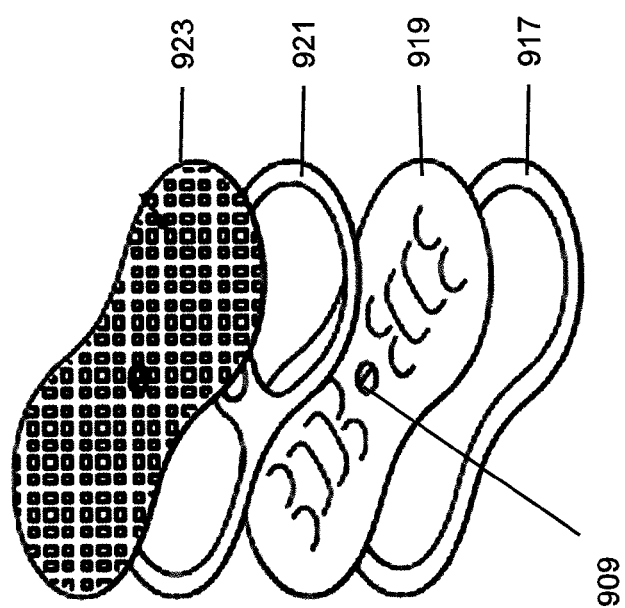

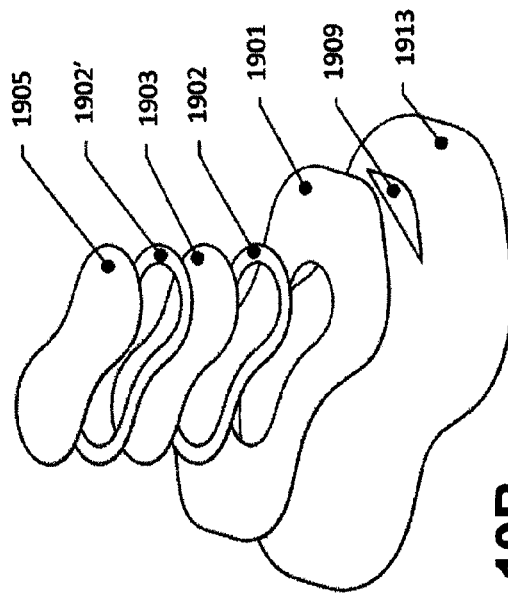
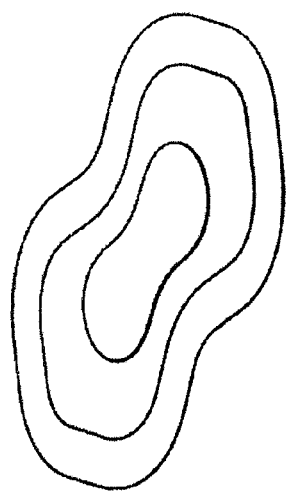
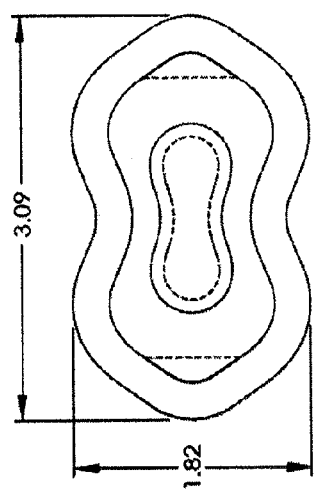
FIG. 19B
FIG. 19C
FIG. 19A

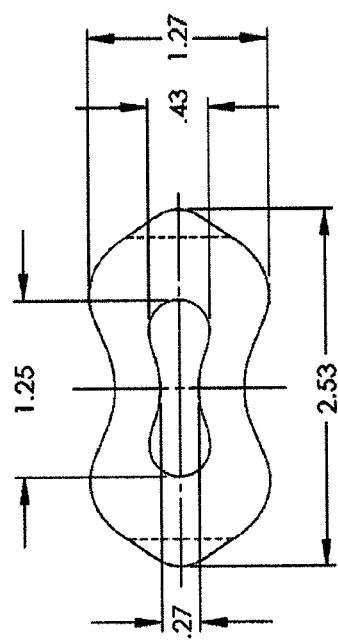
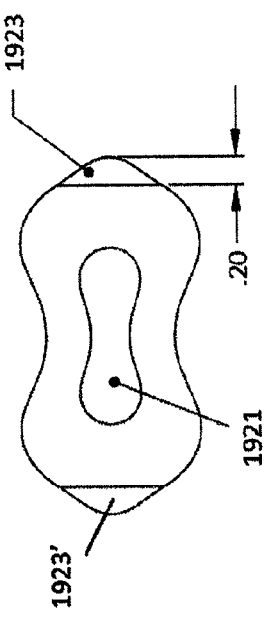
FIG. 21A
FIG. 21B
FIG. 21C

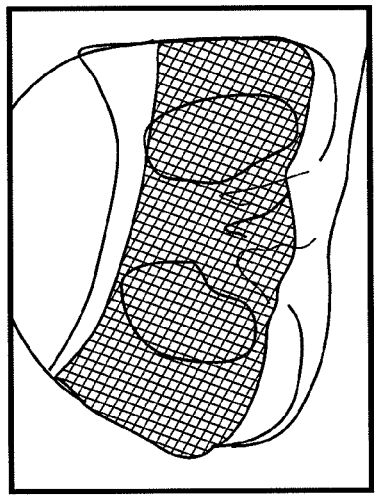
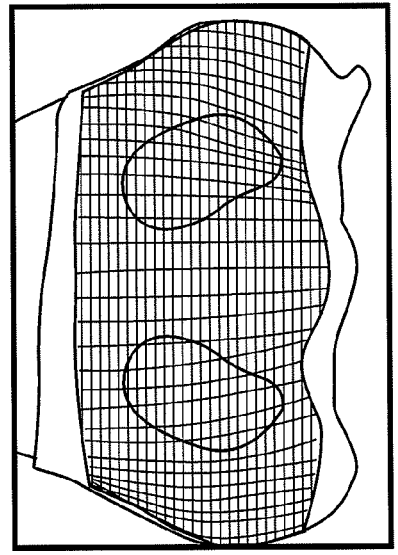
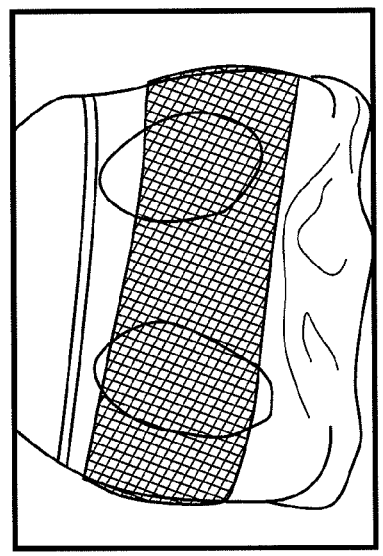
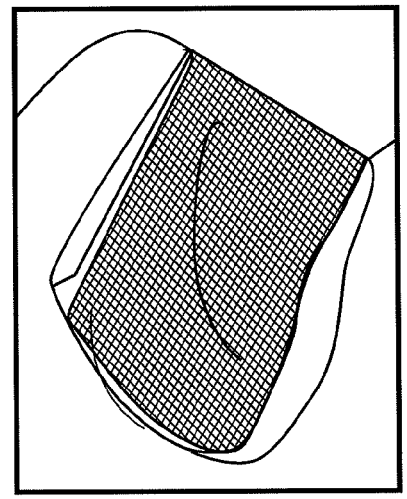
FIG. 27B
FIG. 27D
FIG. 27A
FIG. 27C

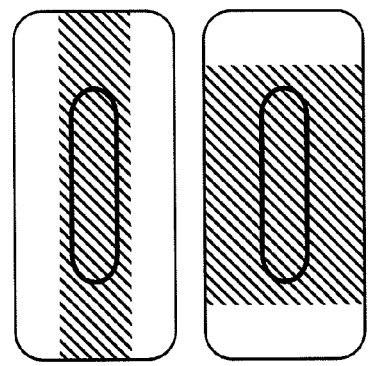
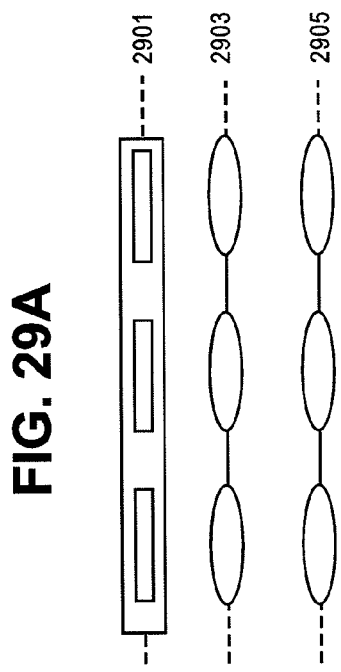
FIG. 29A
FIG. 29B
FIG. 29C

ADHESIVE NASAL RESPIRATORY DEVICES

CROSS-REFERENCE TO RELATED APPLICATIONS

This application is a continuation of U.S. patent application Ser. No. 12/141,875, filed Jun. 18, 2008, titled "ADHESIVE NASAL RESPIRATORY DEVICES", which is a continuation-in-part of U.S. patent application Ser. No. 11/298,339, filed Dec. 8, 2005, titled "RESPIRATORY DEVICES", now U.S. Pat. No. 7,798,148, which claims priority to U.S. Provisional Patent Application Ser. No. 60/634,715, filed on Dec. 8, 2004.

U.S. patent application Ser. No. 12/141,875 is also as a continuation-in-part of U.S. patent application Ser. No. 11/759,916, filed on Jun. 7, 2007, titled "LAYERED NASAL DEVICES".

U.S. patent application Ser. No. 12/141,875 also claims priority to U.S. Provisional Patent Application Ser. No. 61/037,180 filed Mar. 17, 2008, titled "NASAL DEVICES WITH NOISE-REDUCTION AND METHODS OF USE". All of these patent and pending applications are herein incorporated by reference in their entirety.

BACKGROUND

Nasal respiratory devices have been well-described in the following US patent applications, each of which is incorporated herein in its entirety: U.S. patent application Ser. No. 11/298,640, titled "NASAL RESPIRATORY DEVICES", filed Dec. 8, 2005; U.S. patent application Ser. No. 11/298,339, titled "RESPIRATORY DEVICES", filed Dec. 8, 2005; and U.S. patent application Ser. No. 11/298,362, titled "METHODS OF TREATING RESPIRATORY DISORDERS", filed Dec. 8, 2005.

These patent applications generally describe nasal respiratory devices and methods for treating a variety of medical conditions through the use of such devices. These medical conditions include, but are not limited to, snoring, sleep apnea (obstructive, central, complex and mixed), Cheyne Stokes breathing, UARS, COPD, hypertension, asthma, GERD, heart failure, and other respiratory and sleep conditions. Such nasal respiratory devices may passively induce positive end-expiratory pressure ("PEEP") or expiratory positive airway pressure ("EPAP"), and are adapted to be removably secured in communication with a nasal cavity. These devices act passively because they do not actively apply positive airflow, but instead regulate the subject's normal breathing, typically using one or more valves to inhibit expiration more than inspiration.

For example, U.S. patent application Ser. No. 11/759,916 describes passive nasal devices such as that shown in FIG. 1A and 1B. FIG. 1A is a back view of one example of a nasal device formed into a flexible, somewhat "flat" configuration, so that it may be applied over (and/or partially within) a subjects nostril. This example is a layered nasal device, because it may be formed of layers, as shown in FIG. 1B. The device typically includes a holdfast layer 101 and an airflow resistor 103. The reverse side of the device shown in FIG. 1A includes an adhesive material (not visible) that may be covered by a protective covering. The protective covering (which may also be referred to as a protective liner) can be removed to expose the adhesive before application of the device. Thus, the holdfast layer of the device secures it to the subject. This holdfast layer may itself be layered (formed of layers), and may include an adhesive substrate (e.g., a backing layer). FIG. 1B shows an exploded view of the device of FIG. 1A, illustrating the layers of the device, including the adhesive holdfast 101 layer, the airflow resistor layer (comprising the flap valve 107 layer and flap valve limiter 109 layer), and an adhesive ring 111 that may help attach the flap valve and flap valve limiter to the adhesive holdfast.

The layered adhesive nasal devices previously described may be used in communication with one nostril ("single nostril" devices) or both nostrils ("whole-nose" devices). Whole-nose nasal device may be particularly useful, at least because they may be easily applied, have highly predictable expiratory and inspiratory resistances, and are less likely to be affected by nasal cycling, a phenomena in which vasculature in each nasal passage becomes more engorged and then less engorged, leading to variations in each nostril's air flow. The respiratory devices described herein provide additional variations and features of whole-nose nasal devices that may be removably secured at least partly over, at least partly around and/or at least partially within a subject's nose or nostrils. It would be beneficial to provide additional nasal devices (and methods of manufacturing and using such devices), that may be used to passively regulate airflow through both of a subject's nostrils. Such whole-nose nasal devices are described in greater detail and shown in examples below.

SUMMARY OF THE DISCLOSURE

Whole-nose nasal respiratory devices and methods of making and using whole-nose nasal respiratory devices are described and illustrated herein. These devices are typically configured to be adhesively secured to a subject so that they engage both of the subject's nostrils and allow airflow from both nostrils to communicate with an airflow resistor. The airflow resistor is configured so that it inhibits exhalation through the nostrils more than it inhibits inhalation through the nostrils.

For example, described herein are whole-nose nasal respiratory devices having an airflow resistor configured to inhibit exhalation through both nostrils more than inhalation through both nostrils and an adhesive holdfast configured to secure the device in communication with both of a subject's nostrils. The airflow resistor may be a flap valve or a plurality of flap valves. For example, the airflow resistor may include a flap valve layer with multiple flaps that is adjacent to a flap valve limiter layer. The flap valve limiter layer may be a mesh or screen that prevents or limits the flap valve from opening during expiration. For example, the airflow resistor may comprise multiple small flaps extending across the surface of a flap valve layer. One variation may be referred to as a "fish scale" embodiment, in which the flaps resemble fish scales. Other flap shapes may be used, including but not limited to triangular, rectangular, semi-circular shapes, etc.

The airflow resistor (which may include multiple valves) typically communicates with both nostrils. In some variations the device may include a passageway communicating with both nasal openings and the airflow resistor. The airflow resistor may be configured as a surface (e.g., layer) that extends substantially across both of the subject's nostrils (and between them) when worn.

The adhesive holdfast is generally configured to secure the nasal device in communication with the subject's nose. In general, the nasal device is adhesively secured across both of the subject's nostril openings. For example, the adhesive holdfast may be configured to secure the device over both of the subject's nostrils so that the airflow resistor is positioned outside of the subject's nostrils. In some variations a portion of the nasal device may extend into one or both of the subject's nostrils. For example, an aligner (e.g., an alignment protrusion) or centering protrusion may be included to help apply the device, and may be used to help position it. In other variations, the device does not extend into the subject's nose.

The adhesive holdfast may be a substantially flat layer. For example, the adhesive holdfast may be a substantially flat and flexible substrate that includes a biocompatible adhesive. The substantially flat adhesive holdfast typically has a thickness that is much less than the width and height (and surface area) of the device. In some variations the adhesive holdfast surrounds the airflow resistor, so that it can seal against the subject's nostrils and allow airflow through the nostrils to pass through the airflow resistor. The adhesive holdfast may be adapted to conform to the area around a subject's nostril openings. For example, the adhesive holdfast may have an elongate length in the outer perimeter that includes a narrower region (e.g., a recessed, concave or curved region of the outer perimeter) so that the adhesive holdfast may secure to the upper lip region. In one variation, the holdfast is configured as an elongated strip surrounding the airflow resistor. In some variations the adhesive holdfast is an elongate rectangular shape, with the airflow resistor in the center of the device. In some variations, the adhesive holdfast has a two-lobed (e.g., Figure "8") shaped perimeter.

Any of the nasal devices described herein may include one or more openings or leak pathways that are open to airflow during both exhalation and inhalation. For example, the opening may be a hole or passage through the airflow resistor and/or the adhesive holdfast that is always open. In some variations, more than one opening is present. The size and/or position of the opening may be chosen so that the resistance to expiration and/or the resistance to inspiration falls within a predetermined range, as described in greater detail below.

The whole-nose nasal devices described herein typically have a resistance to expiration that is greater than the resistance to inspiration. In general, the whole-nose nasal devices described herein may have a resistance to expiration that is between about 1 and about 250 cm $H_2O$/L/sec. In some variations, the resistance to expiration is between about 5 and about 250 cm $H_2O$/L/sec. The whole-nose nasal devices described herein may have a very low resistance to inspiration. For example, the resistance to inspiration may be between about 0.01 and about 5 cm $H_2O$/L/sec.

Any of the nasal devices described herein may also include one or more of: a protective cover for holdfast, tabs for gripping/applying the device, a guide (e.g., aligner) to aid in applying the device, a spacer component for spacing the device (and particularly the airflow resistor) from nose, and a frame or support/stiffening member.

A protective cover may be a paper, plastic, or other material that may at least partially cover the adhesive of the holdfast to protect it until the device is applied to a subject. The protective cover may be multiple pieces that may be removed all at once, or in multiple steps. In some variations the protective cover is removed by unpeeling it from the adhesive.

The device may also include one or more tabs and/or grips for grasping the device to help apply or remove the device from the subject's nose. A tab may also help secure the device. For example, the tab may be configured as a portion (particularly an edge region) of the adhesive holdfast that does not include an adhesive on the side of the device that will adhere to the subject's face. The tab or grip region may extend from the perimeter of the device. The tab may be removable after the device is secured to the subject, or it may be part of the device that is not removable. More than one tab (e.g., one on either side of the device) may be present. In some variations the tab or grip extends from the holdfast and is removable after the device is applied to the subject.

As mentioned above, a guide or aligner may be used to align the device with the subject's nose or nasal openings. In general the whole-nose nasal devices described herein may not require an aligner because the airflow resistor and/or any passageway in which the airflow resistor is located is sufficiently large so that precise alignment is unnecessary. For example, the airflow resistor may be an airflow resistor layer that is elongate, and extends longer than the distance between the right and left alar regions of the nose (i.e., the base of the nose having the nostril openings).

In some variations, a spacing or spacer component ("spacer") for spacing the device from the nasal openings may also be included. For example, a spacer may be a protrusion or bridge region that extends from the nasal device to space the nasal device (and particularly the airflow resistor) from the nose or nasal openings of the nose. The spacer may be configured to contact the edge of the nose (i.e., alar region or the columella region between the nostrils). The spacer may also include an adhesive, or may be non-adhesive.

Any of the devices described herein may also optionally include a frame or support/stiffening member. The frame (which may also be referred to as a support member) may be particularly useful for very thin or very flexible holdfast regions. For example, the support member may help prevent the edges of the adhesive holdfast region from folding back on themselves during application. The frame may be made of a material that is also flexible, but is either thicker or otherwise results in a stiffer assembly than the adhesive holdfast alone. The support frame may also be configured to help secure the device to the subject. For example, the support frame may be shaped similar to the subject's nasal region. The support frame may be removable (e.g., after the device has been applied to the subject), or it may be left on as part of the nasal device.

In some variations, the device may include a rim or rim body forming a passageway which is regulated by the airflow resistor. The rim may be formed of a separate material, or it may be formed by the structures of the holdfast and/or the airflow resistor(s). For example, the rim may be present along or near the inner periphery of the adhesive holdfast and provide structural support and surround and/or define the passageway. This rim may be formed from other layers of the adhesive device that when combined, provide a rim structure. Alternatively, the rim may be a separate component that is added to the device. In some cases, the rim facilitates the attachment of a sensor, such as a nasal cannula, thermistor, thermocouple or other device that provides information about the device and/or the subject wearing the device. The rim can be flexible or rigid, and can be completely or partly circumferential. Thus, a rim may include the portion of the device that surrounds the passageway and/or resistor and provides structural support to protect the passageway. In some variations the rim is formed of two or more portions that are connected together. For example, a rim body may be formed of an upper and lower rim body that are joined together. The holdfast may be secured between the two, and the airflow resistor may be aligned within the passageway of the rim body.

Also described herein are whole-nose nasal respiratory devices including: an airflow resistor configured to communicate with both nostrils and to inhibit exhalation through both nostrils more than inhalation through both nostrils; a flexible, elongate adhesive holdfast surrounding the airflow resistor and configured to secure the airflow resistor in communication with both of the subject's nostrils; a frame in communication with an outer edge of the adhesive holdfast, wherein the frame is configured to support the adhesive holdfast; and an opening through the device that is open to allow airflow through the device during both exhalation and inhalation.

In some variations, the whole-nose nasal respiratory devices comprise: a flexible, elongate holdfast layer having a non-rectangular outer perimeter and comprising a biocompatible adhesive; a flap valve layer comprising a plurality of flap valves, wherein the flap valve layer is at least partially surrounded by the elongate holdfast substrate layer; a flap valve limiter layer adjacent to the flap valve layer and configured to limit the opening of the flap valves so that the device inhibits exhalation more than inhalation through both nostrils; wherein the whole-nose nasal respiratory device is configured to be substantially flat and flexible, and is further configured to be worn in communication with both of the subject's nostrils. The outer perimeter may include a recessed region. The non-rectangular outer perimeter may be curved and may include lobes. For example, the perimeter may have two symmetric lobes. In some variations the non-rectangular outer perimeter is lentiform (biconvex).

Also described herein are whole-nose nasal respiratory devices that include an airflow resistor configured to inhibit exhalation through both nostrils more than inhalation through both nostrils, a flexible, adhesive holdfast surrounding the airflow resistor and configured to secure the airflow resistor in communication with both of the subject's nostrils; and an opening through the device that is open to allow airflow through the device during both exhalation and inhalation. As mentioned, the airflow resistor may include a flap valve layer adjacent to a flap valve limiter layer. Similarly, the adhesive holdfast may include a substrate layer and a biocompatible adhesive. In some variations, the adhesive holdfast is substantially flat and elongate. For example, the holdfast may have an outer perimeter that is curved ("C" shaped, "8" shaped, etc.). In some variations, the outer perimeter of the adhesive holdfast includes an inwardly curving region near the midline of the device.

Also described herein are whole-nose nasal respiratory devices including an elongate holdfast substrate layer comprising a biocompatible adhesive, a flap valve layer comprising at least one flap valve (wherein the flap valve layer is at least partially surrounded by the elongate holdfast substrate layer), a flap valve limiter layer adjacent to the flap valve layer and configured to limit the opening of the flap valve(s) (for example preventing opening of the valve in the direction away from the subject's nose) so that the device inhibits exhalation more than inhalation through both nostrils. The whole-nose nasal respiratory device is typically substantially flat and flexible, and is further configured to be worn in communication with both of the subject's nostrils. In some variations, the device also includes one or more openings (leak pathways) that are open during both inspiration and expiration.

Also described herein are methods of applying a whole-nose nasal respiratory device, including the steps of: removing a protective covering layer from at least part of a whole-nose nasal respiratory device, wherein the whole-nose nasal respiratory device comprises an airflow resistor configured to inhibit exhalation through both nostrils more than inhalation through both nostrils and an adhesive holdfast configured to secure the device in communication with both of a subject's nostrils; and adhesively securing the holdfast of the nasal respiratory device at least partly over both of a subject's nostrils.

The step of adhesively securing the nasal respiratory device may include sealing the adhesive holdfast of the nasal respiratory device to or around the subject's nose or skin. The step of removing the protective layer comprises unpeeling the protective layer from the whole-nose respiratory device.

In some variations of the methods of applying a whole-nose nasal respiratory device, the method includes the steps of: removing a protective covering layer from at least part of a whole-nose nasal respiratory device, wherein the whole-nose nasal respiratory device comprises an airflow resistor configured to inhibit exhalation through both nostrils more than inhalation through both nostrils and an adhesive holdfast layer configured to secure the device in communication with both of a subject's nostrils, aligning the whole-nose nasal respiratory device with the subjects nose so that a recessed region on the outer perimeter of the holdfast layer aligns with the space between the subject's nostrils; and adhesively securing the holdfast of the nasal respiratory device at least partly over both of a subject's nostrils.

INCORPORATION BY REFERENCE

All publications and patent applications mentioned in this specification are herein incorporated by reference in their entirety as if each individual publication or patent application was specifically and individually indicated to be incorporated by reference.

BRIEF DESCRIPTION OF THE DRAWINGS

FIG. 4A shows an exploded view of one variation of an airflow resistor comprising a flap valve layer and a flap valve limiter layer. FIG. 4B shows a top perspective view of the airflow resistor of FIG. 4A assembled so that the flap valve layer is adjacent to the flap valve limiter layer.

FIG. 4C and FIG. 4D show cross-sectional views taken through the airflow resistor of FIG. 4B (line A-A') during inhalation and exhalation, respectively.

FIGS. 7A to 7P show variations of flap valve airflow resistors that may be used with whole-nose nasal devices.

FIGS. 8A to 8o show variations of flap valve airflow resistors that may be used with whole-nose nasal devices.

FIG. 9E is an exploded view of one variation of an airflow resistor that may be part of a whole-nose nasal device.

FIG. 19A is a front view of one variation of a whole-nose nasal device. FIG. 19B is a perspective view of the device of FIG. 19A, and FIG. 19C is an exploded view of the device of FIG. 19A.

FIG. 21A is a front view of the adhesive holdfast of the device of FIGS. 19A-19C, showing the side of the device not facing the subject when the device is worn. FIG. 21B is a side view of the adhesive holdfast shown in FIG. 21A, and FIG. 21C is a back view. The dimensions shown are merely examples of dimensions that may be appropriate.

FIGS. 27A-27D illustrate variations of adhesive nasal devices applied to a subject's nose.

FIG. 29A illustrates one method of manufacturing an adhesive nasal device and FIGS. 29B and 29C show whole-nose nasal devices manufactured as continuous strips.

DETAILED DESCRIPTION

Figure 1B:
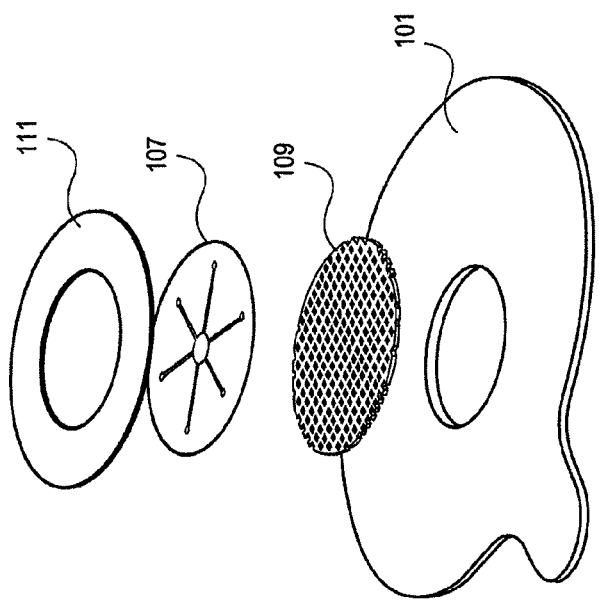
FIGS. 1A and 1B show one variation of a single-nostril adhesive holdfast in a back view and an exploded perspective view, respectively.

Described herein are whole-nose adhesive nasal respiratory devices generally including an airflow resistor and an adhesive holdfast that is configured to secure the device in fluid communication both of a subject's nostrils. Whole-nose nasal respiratory devices may be used to regulate a subject's respiration. For example, the device may create positive airway pressure ("PAP"), including positive end expiratory pressure ("PEEP") or expiratory positive airway pressure ("EPAP") during respiration in a subject wearing the device. The adhesive respiratory devices and methods described herein may be useful to treat a variety of medical conditions, and may also be useful for non-therapeutic purposes. The devices and methods described herein are not limited to the particular embodiments described. Variations of the particular embodiments described may be made and still fall within the scope of the disclosure. Examples and particular embodiments described are not intended to be limiting.

As used herein, a whole-nose nasal device may be configured to fit across, partly across, at least partly within, in, over one and/or both of a subject's nostrils. These whole-nose nasal devices may be referred to herein as "adhesive nasal devices." Layered nasal devices are of particular interest, and are described more fully below. Layered adhesive nasal devices may include two or more layers. For example, a layered nasal device may include an adhesive holdfast layer and an airflow resistor layer. These layers may be composed of separate layers, and these layers may be separated by other layers, or they may be adjacent. The adhesive holdfast layer may be itself formed of layers (optionally: a substrate layer, a protective covering layer, an adhesive layer, etc), and thus may be referred to as a layered adhesive holdfast. Similarly, the airflow resistor may be formed of multiple layers (optionally: a flap valve layer, a valve limiter layer, etc.), and thus may be referred to as a layered airflow resistor. In some variations, the layered adhesive holdfast and the layered airflow resistor share one or more layers. For example, the flap valves layer and the adhesive substrate layer may be the same layer, in which the leaflets of the flap valve layer are cut from the substrate layer material. As used herein, a "layer" may be generally planar geometry (e.g., flat), although it may have a thickness, which may be uniform or non-uniform in section.

As used in this specification, the singular forms "a," "an," and "the" include plural reference unless the context clearly dictates otherwise. The following descriptions include various design parameters or goals, and methods and devices which fit the design parameters or goals. The devices and methods described herein (and recited by any claims) are not limited to any particular theory of operation.

In general, the whole-nose nasal devices described herein include a holdfast region (or layer) and at least one airflow resistor. As will be apparent from the figures, many of these devices may be removed (removable) and applied by a user without special tools. In some variations, a subject may use an applicator to apply the device (e.g., to help align it).

In addition to the airflow resistor and the holdfast, any of the whole-nose nasal devices described herein may also include one or more of: a protective cover for the adhesive holdfast, an opening or leak pathway, tabs and/or grips to apply the whole-nose nasal device, an aligner for aligning the device, a spacing or spacer component ("spacer"), and a frame or support/stiffening member. These features are described briefly below, and illustrated in the accompanying drawings.

In operation, a whole-nose nasal device is applied so that the airflow resistor is placed in communication with both of a subject's nostrils to modify the flow of air through the subject's nose. Thus, the respiratory devices are configured so that airflow from both nostrils is received by the airflow resistor. In variations having multiple airflow resistors (or in which the airflow resistor includes multiple valves), each airflow resistor receives airflow from both nostrils. For example, the airflow from each nostril may be combined prior to contacting the airflow resistor. Thus, in some variations the devices include a passageway that is configured to communicate with both nostrils before reaching the airflow resistor(s).

The airflow resistor typically modifies the flow of air through the nose in at least one direction. In most variations of the devices described herein, the airflow resistor is configured to resist airflow through the device in one direction more than it resists airflow in the opposite direction. For example, an airflow resistor may occlude airflow during exhalation more than inhalation. Resistance to inhalation may be increased minimally, negligibly, or not at all. Examples of airflow resistors are described below, but any appropriate airflow resistor may be used. For example, airflow resistors may be valves for regulating airflow (e.g., flap valves, hinge-less valves, balloon valves, stepper valves, ball valves, etc.) or the like. In the examples shown in the figures and described herein, the airflow resistor is typically a flap valve having one or more flaps or leaflets that move to regulate flow through the resistor. The airflow resistor may also include a valve limiter, such as a flap valve limiter. A valve limiter (e.g., flap valve limiter) restricts the ability of a valve to open in one or more directions. As described in more detail below, the flap valve limiter may prevent the valve from substantially opening in one direction (e.g., expiration) or may allow some degree of opening or partial opening, but not complete opening Any of the nasal devices described herein may also include one or more openings, which may also be referred to as leak pathways, through which air can pass when the valve is otherwise closed. The leak pathway may be separate from the airflow resistor, or it may be part of the airflow resistor (e.g., passing through a region of the flap valve, etc.). In some variations, the airflow resistor is configured so that a leak pathway is formed when the valve is closed. For example, the flap(s) of the flap valve may not completely seal when the valve is closed, thus providing an intentional or unintentional leak path. A leak pathway may pass through any appropriate region of the device, including the holdfast region.

A whole-nose nasal device may be configured to treat snoring, or sleep disordered breathing such as sleep apnea, as described briefly above. For example, a subject may apply a whole-nose adhesive respiratory device to his nose by exposing the adhesive on the holdfast of the device (e.g., by removing a protective cover material from an adhesive region of the holdfast) and applying gentle pressure to adhere the device around the nostrils. In this way, the device may be seated around the nasal orifice and form at least a partial seal between the nostrils and the device so that the majority of flow into and out of the nostrils passes through the device and/or airflow resistor. Once the device is applied to the subject's nose, respiration through the nostrils may be regulated. In some variations, the adhesive nasal device is configured so that there is only nominal resistance through the nasal device during inhalation (e.g., less than about 0.1 cm $H_2O$/L/sec, less than about 0.5 cm $H_2O$/L/sec, less than about 1 cm $H_2O$/L/sec, and less than about 5 cm $H_2O$/L/sec), but increased resistance to airflow during exhalation (e.g., greater than about 1 cm $H_2O$/L/sec, greater than about 5 cm $H_2O$/L/sec, greater than about 10 cm $H_2O$/L/sec, and greater than about 20 cm $H_2O$/L/sec, greater than about 50 cm $H_2O$/L/sec, etc.). In some variations the airflow resistor may have an upper limit on the expiratory resistance. For example, the expiratory resistance may be between about 1 and about 250 cm $H_2O$/L/sec, or between about 2 and about 100 cm $H_2O$/L/sec, etc. The resistance to inspiration and/or expiration may be determined based on the configuration of the airflow resistor and/or any leak pathway(s). A subject wearing the device may still breathe predominantly though the nose (and the nasal device) during exhalation, but may also breathe at least partly through the mouth.

It may also be beneficial for a subject to wear a whole-nose nasal respiratory device when sleeping. Described below are variations of whole-nose nasal devices (including layered nasal devices) that may be comfortably worn and secured in or over the subject's nose so that the subject may sleep. In some variations, a grip (e.g., a tab, handle, strap, or other additional interface region) may be included to help secure the device to the subject's, and may additionally or alternatively be helpful in positioning or manipulating (e.g., gripping) the device, particularly when it is being applied. This additional interface region may be formed of the same material as the adhesive holdfast region, or it may be a separate region, as described in more detail below.

In some embodiments, one or more components of the device is impregnated with, contains, or is coated with, one or more compounds that may be inhaled during use. The presence of airflow, heat or other conditions may facilitate the release of the compound into the inhaled air or surrounding tissues. The compound may be herbal (such as menthol or lavender), chemical or pharmaceutical (such as an antihistamine or anti-asthma drug). Depending on the compound, the user might experience a pleasant aroma (which may soothe or promote sleep or activity) or medical benefits, such as promoting nasal decongestion or asthma relief. The compound may be inhaled during all or at least a portion of the time the user is wearing the device. The compounds may be used as part of treatment of a sleep apnea, snoring, or may find use in other embodiments for other medical conditions.

In some versions, the device is used with an active agent. In some versions, the active agent comprises a drug. An active agent (e.g., a medicament) or other compound can be placed in or on the device to deliver the active agent into the mouth, tongue, hard and soft palates, sinuses, nose, nasal cavity, pharynx, vocal cords, larynx, airways, lungs, trachea, bronchi, bronchioles, alveoli, air sacs, or any tissues that are exposed to inspiratory or expiratory airflow. In some cases, the active agent may be embedded or impregnated in the device or components of the device. In some cases the active agent is a coating. An active agent may comprise any compound that is in some way useful or desirable for the patient. For example, the active agent may be any odorant, including: menthol, phenol, eucalyptus, or any agent that provides a fragrance in the inspired air. Alternatively, an active agent may comprise a drug with beneficial effects, such as beneficial vasculature effects. For example, an active agent may comprise a drug that affects the blood vessels (oxymetazoline or any other vasoactive compound), nasopharynx, airways or lungs (albuterol, steroids, or other bronchoconstriction or bronchodilation compounds). An active agent may comprise, for example, an antibiotic or a steroid. The above list of active agents is not meant to be limiting.

Figure 1A:
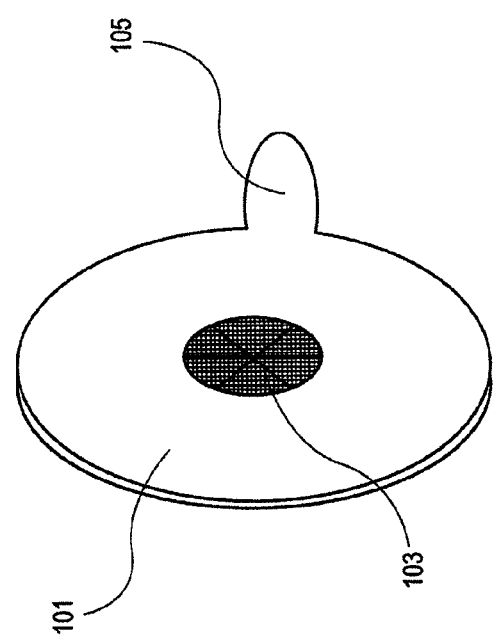

Whole-nose nasal devices as described herein may be preferred when compared to single-nostril nasal devices such as those illustrated in FIGS. 1A and 1B, although they may include similar (or identical) elements, as described briefly above. In particular, a whole-nose nasal device may be easily applied. For example, a whole-nose nasal device may be applied without requiring an aligner. For example, the airflow resistor region (or passageway region) may be sized to tolerate variations in the positioning or alignment of the device on the subject's nose.

The whole-nose nasal devices described herein are typically flexible (i.e., bendable) devices. Overall, the devices may have an elongate, flattened appearance and may be applied across both of a subject's nostrils. The device maybe configured to secure around the subject's nasal openings (e.g., to the outer surface of the subject's nose and/or the apron of the upper lip, etc.). In some variations the device may also project into the nostrils; in other variations the device does not project into the nostrils.

Figure 2A:
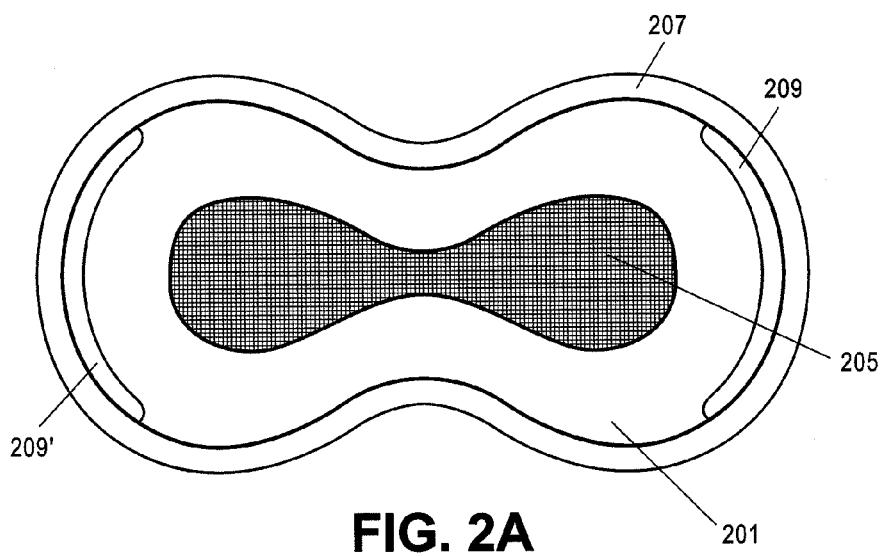
FIG. 2A is a front view of one variation of a whole-nose nasal device.

FIG. 2A shows one variation of a whole-nose nasal device, shown in front view. The front view is the side of the nasal device which will face away from the subject when the device is worn. In FIG. 2A, the whole-nose nasal device is a layered nasal device that is formed of a holdfast layer 201 including a biocompatible adhesive (not visible in FIG. 2A). The holdfast region 201 surrounds the airflow resistor 205. In this example the airflow resistor is a layered airflow resistor including a flap valve layer (not visible) and a valve limiting layer. In FIG. 2A, the valve limiting layer is a mesh that is adjacent to the flap valve. A protective cover 207 is shown attached to the adhesive holdfast 201, protecting the adhesive surface until the cover 207 is removed to expose the adhesive so that the device can be applied. A portion 209, 209' of the holdfast facing the subject on either on either side of the device does not include an adhesive, which may help in removing the protective cover from the device.

The overall shape of the device shown in FIG. 2A is an elongate flattened strip. The thickness of the device (along its thinnest edge) is dependent upon the thickness of the layers (the holdfast layers, the airflow resistor layers, etc.) making up the device, but can be fairly thin, helping keep the device flexible. The shape of the face of the device (surfaces forming the front and back of the device) in FIG. 2A is curved, and generally "8" shaped, having an inwardly-curving perimeter near the midline. This curved center region may help the device fit a subject's face.

Figure 2B:
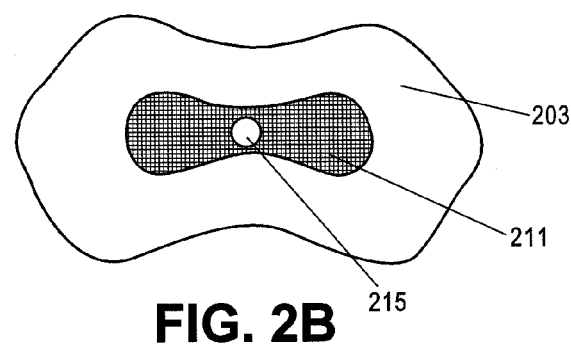
FIGS. 2B and 2C are back views of two variations of a whole-nose nasal device, showing the side of the device configured to adhesively contact a subject.
Figure 2C:
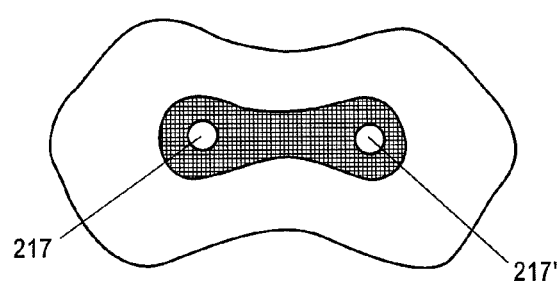

FIGS. 2B and 2C show back views of other variations of whole-nose nasal devices similar to the device shown in FIG. 2A. The back surface of the devices shown in FIGS. 2B and 2C include the adhesive side of the holdfast 203 that is configured to contact a subject wearing the devices. A transparent valve layer 211 making up part of the airflow resistor 205 is also visible. In FIG. 2B, the whole-nose device also includes an opening 215 or leak pathway in the center of the device, passing through the airflow resistor. Similarly, the whole-nose device of FIG. 2C includes two small leak pathway openings 217, 217'.

Figure 3A:
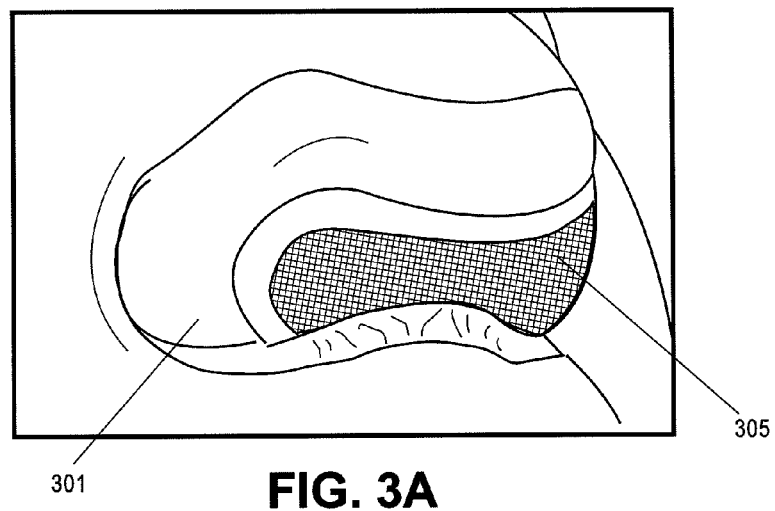
FIGS. 3A and 3B show perspective views of whole-nose nasal devices applied to a subject.
Figure 3B:
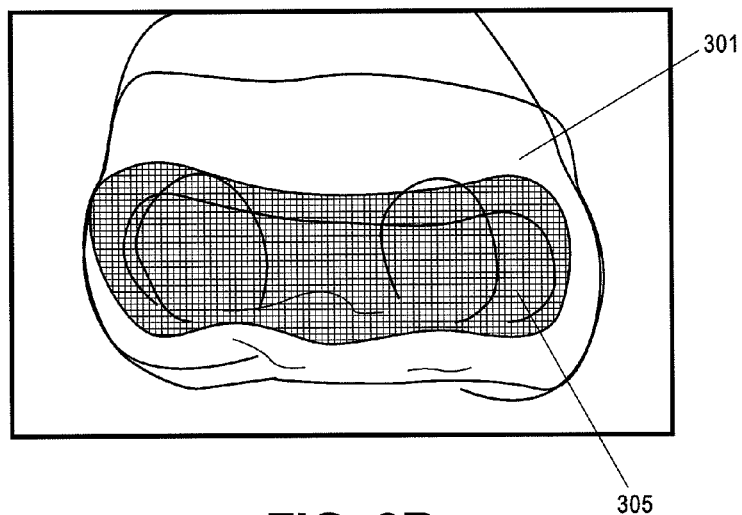

FIGS. 3A and 3B illustrate whole-nose nasal devices that are adhesively secured so that the airflow resistor layer 305 is in communication with both of the subject's nostrils. Both of these examples include adhesive holdfasts 301 that surround the airflow resistor 305 and adhere to the skin around the subject's nose. In this example, the adhesive holdfast is formed from a clear polymeric material.

The exemplary devices shown in FIGS. 2A to 3B all show airflow resistors that inhibit expiration more than inspiration through the nose, when the devices are worn.

Airflow Resistors

Any appropriate airflow resistor may be used as part of the adhesive nasal devices described herein. The airflow resistors described herein typically restrict airflow in one direction more than they restrict airflow in the opposite direction. An airflow resistor typically occludes airflow during exhalation more than inhalation. Examples of airflow resistors may be found in published U.S. patent application Ser. No. 11/298,640, titled "NASAL RESPIRATORY DEVICES" (filed Dec. 8, 2005), herein incorporated by reference in its entirety.

In some embodiments, the pressures created by the airflow resistor during exhalation may be between 0.01 and 100 cm of $H_2O$ measured at a flow rate of 100 ml/sec (e.g., 0.1 cm $H_2O$/L/sec and 1000 cm $H_2O$/L/sec). The whole-nose nasal device may be configured so that the overall resistance to exhalation through the device is between about 5 and about 250 cm $H_2O$/L/sec. The resistance to inhalation for the whole-nose nasal devices is always less than the resistance to exhalation, and is typically between about 0.1 cm $H_2O$/L/sec and about 5 cm $H_2O$/L/sec. The resistance to inhalation and the resistance to exhalation for the whole-nose nasal device may be set based on the configuration of the airflow resistor and the configuration of any leak pathways. A leak pathway is typically an opening through the device that is open during both exhalation and inhalation. The resistance to the airflow resistor may be adjusted by one or more leak pathways so that the overall resistance (airflow resistance) of the device is within the desired range.

In some variations of the adhesive devices described herein adapted to be used to treat snoring, the airflow resistor creates a resistance to exhalation that is relatively low. For example, the resistance to exhalation may be between about 0.5 cm of $H_2O$/L/sec and about 100 cm $H_2O$/L/sec, or between about 20 cm $H_2O$/L/sec and about 80 cm $H_2O$/L/sec, or between about 30 cm $H_2O$/L/sec and about 80 cm $H_2O$/L/sec, or about 40 cm $H_2O$/L/sec.

Valve-type airflow resistors are particularly suitable. In particular, valves that may be used include flap valves (having one or more flaps or leaflets), hingeless valves, stopper-type valves, membrane-type valves, ball valves, balloon-type valves, and the like. This list is not intended to be exhaustive, and other types of selective airflow resistors may be used. Moreover, multiple airflow resistors may also be used, which may include combinations of different types of airflow resistors. Flap valves are of particular interest. An airflow resistor configured as a flap valve typically includes one or more hinged or flexible flaps (or leaves) that is movably secured so that the flap may open when air flows in one direction, and close when air flows in the opposite direction, or when air is not flowing. The opening and closing of the flap may allow air to flow across the valve, and thereby regulate airflow through the device. In operation, the flap portion of the flap valve can thus selectively occlude airflow in one direction more than in other directions.

In some variations, the airflow resistor is positioned within a passageway. The passageway typically communicates with both nasal openings, so that airflow from both nostrils communicates with the airflow resistor.

Valves configured for PEEP (positive end expiratory pressure) may also be used with any of the devices described herein. For example, a valve may be configured to have a non-zero threshold pressure for opening during expiration so that the valve is closed during expiration when the pressure across the valve is below the threshold pressure for opening during expiration, but the valve opens during expiration when the valve exceeds the threshold pressure for opening during expiration.

In some variations, an airflow resistor for use in an adhesive respiratory device includes a flap valve and a flap valve limiter that limits the movement of the flap valve. For example, a flap valve may be a flexible material (e.g., silicone or a flexible polymer) that can bend or flex to create an opening for airflow during inspiration (in a first direction). The flap valve may be prevented from opening for airflow during exhalation (in a second direction) by a flap valve limiter. Thus, a flap valve limiter may be a structure having a flap valve engagement surface (such as a bar, post, mesh, matrix or webbing, etc.) that limits the flap valve from opening in the second direction. In some variations, the flap valve limiter is a tether or hinge that is connected to the flap and prevents it from substantially extending beyond a predetermined position. Other flap valve limiters may be configured as valve supports (e.g., cross-bars) that prevent the valve from collapsing when air flows in one direction through the passageway. The airflow limiter may also include a valve seal region (e.g., a rim or ridge or other structural support) against which the flap may be seated or abut when the valve is "closed."

The flap of a flap valve may be made of a flexible material, or a hinged stiff material. In some variations, the flap comprises a thin sheet of flexible material that is shaped to fit across an opening and at least partially occlude airflow through the opening when the flap is closed. The flap may be shaped so that it does not occlude airflow through one or more leak pathways.

FIG. 4A illustrates an exploded view of one variation of an airflow resistor 400 that is a flap valve type airflow resistor including multiple flaps. In FIG. 4A, the airflow resistor 400 is formed by two adjacent layers: a flap valve layer 401 that is adjacent to a flap valve limiter layer 403. The flap valve layer is formed of a flexible sheet of material (e.g., polymeric material) into which, in this example, 14 individual flaps 407 have been cut. An opening 415 (leak pathway) is also present in the flap valve layer.

As mentioned above, one or more leak pathways may be included as part of the adhesive respiratory device. A leak pathway typically allows air to flow through the passageway even when the valve is closed. Thus a minimum basal level of airflow may be permitted through the passageway regardless of the state of the airflow resistor. In some variations, the leak pathway is a hole or un-occluded passage. A leak pathway may be a part of any region of the nasal respiratory device. For example a leak pathway may be part of the airflow resistor, part of the holdfast (or some combination thereof). In some embodiments, the leak pathway arises from an intentional lack of perfect sealing or abutment of various components of the device (e.g., between leaflets of a flap valve, etc) or with the subject's skin. A nasal respiratory device may be configured to have multiple leak pathways.

The flap valve limiter layer shown in FIG. 4A is a mesh layer. As described above, a flap valve limiter is typically an air-permeable structure that limits the range of motion of the flap valve, preventing it from opening (or limiting it to partially opening) in at least one direction. For example, the flap valve limiter may be a mesh, grid, bar, peg, or other structure that does not substantially inhibit the passage of air, but can limit the movement of the flap valve leaflet(s) in at least one direction. A flap valve limiter may be formed in any appropriate manner, including molding (e.g., injection molding), cutting (e.g., die cutting, stamping, laser cutting, etc.) or thermosetting. In some variations the flap valve limiter is a flap valve layer that is formed from a mesh. Thus, the flap valve limiter may be formed by cutting, molding, etc. For example, a flap valve limiter may be formed by cutting a mesh material. A flap valve limiter may limit the movement of the flap valve by supporting the valve leaflets (flap valve leaflets). In other variations, the valve leaflets may be supported along their entire surface (e.g., when the flap valve limiter is a mesh), or at their edges.

A flap valve limiter may be formed of any appropriate material. For example, the flap valve limiter may be formed of a flexible mesh of nylon or other fibrous materials. As briefly mentioned above, the valve limiter may be made of any appropriate air permeable material and may have any appropriate airflow permeable shape. Although it may be beneficial to include materials that are flexible (e.g., nylon mesh), in some variations, it may be beneficial to use materials that are relatively stiff. Exemplary meshes may include: molded polypropylene plastic mesh (e.g., 0.0140" thickness), precision woven nylon mesh (31.2 openings per inch×31.2 openings per inch), precision woven nylon mesh (80×80), precision woven polypropylene mesh (69×69), filter mesh, precision woven nylon mesh (198×198), PTFE diamond mesh, precision woven polyester mesh (109×109), precision woven polyester mesh (45.7×45.7), etc.

In some variations, the flap valves or the flap valve limiter (or both) are coated with a material to increase or decrease friction between the two layers (e.g., to prevent the flap leaflets from sticking to each other and/or to the flap valve limiter). In some variations of the airflow resistor, the flap layer (forming the flap valves) is positioned immediately adjacent to a layer forming the flap valve limiter, as shown in FIG. 4A. However, the flap valve layer and the airflow resistor layers may not be immediately adjacent. For example, there may be an intermediate layer.

FIG. 4B shows a back view of the airflow resistor of FIG. 4A. The "back" or "front" direction typically refers to the direction with respect to the overall device when it is applied to a subject. For example, the whole-nose devices are configured so that the back of the device is worn against the subject, and a portion of the back of the device contacts the subject. The "back" side of the device may also be referred to as the subject-contacting side, or the proximal (relative to the subject) side. Similarly, the front side of the device may be referred to as the distal side.

FIGS. 4C and 4D show cross-sections through the airflow resistor of FIG. 4B (through line A-A') during both inhalation (FIG. 4C) and exhalation (FIG. 4D). In FIG. 4C, inhalation draws airflow through the airflow resistor, so that air (represented by the arrows) opens the flap valves 407, 407' and enters the nostrils. Air also passes through the leak pathway 415 in the center of the airflow resistor. During exhalation, as shown in FIG. 4D, the flap valves are closed against the flap valve limiter 403, and airflow through the device (arrow) is primarily through the central leak pathway 415. It should be noted that in some cases, the leak path includes a hole within the flap valve limiter, but in other cases, there is not a separate hole cut or otherwise present within the flap valve limiter. In some variations, air can pass through the flap valve limiter since it is porous (e.g., it is made of mesh or the like).

Figure 5A:
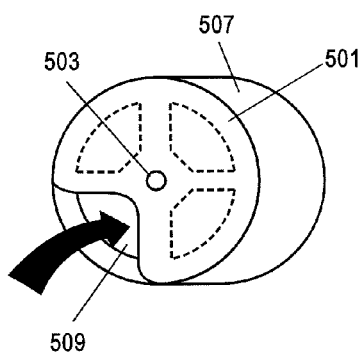
FIGS. 5A and 5B show another variation of an airflow resistor during exhalation and inhalation, respectively.
Figure 5B:
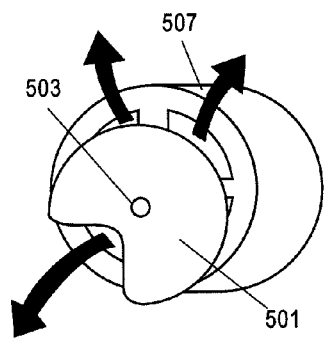

As mentioned, any appropriate type of airflow resistor may be used, including airflow resistors that are not layered. For example, FIGS. 5A-6B illustrate other types of airflow resistors including a pronounced passageway region which valve portion of the airflow resistor communicates with. For example, FIGS. 5A and 5B show an airflow resistor having a membrane 501 (which may be stiff or flexible) that is attached (e.g., by a connector 503) to a body region 507 including a passageway. During exhalation, shown in FIG. 5A, the membrane is held across the passageway and airflow is limited through the opening 509, as indicated by the inward arrow. During inhalation, shown in FIG. 5B, the membrane is deflected from the passageway, so that airflow may pass around the membrane, as illustrated by the arrows. This airflow resistor may be part of a whole-nose nasal device, such as the variation shown in FIG. 5C.

Figure 5C:
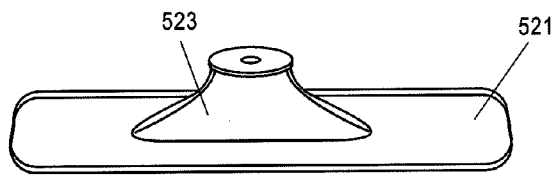
FIG. 5C is a perspective view of another variation of a whole-nose nasal device.

FIG. 5C shows a side perspective view of a whole-nose nasal device including an adhesive holdfast region 521 that surrounds an airflow resistor 523. The airflow resistor include a body region having a passageway that communicates with both nostrils so that airflow to and from the device passes through the valved portion of the airflow resistor.

Figure 6A:
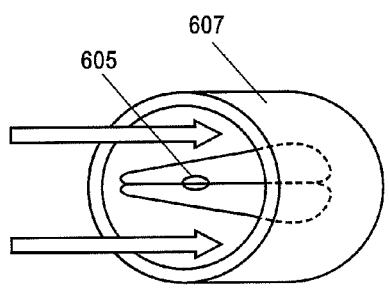
FIGS. 6A and 6B show another variation an airflow resistor during inhalation and exhalation, respectively.
Figure 6B:
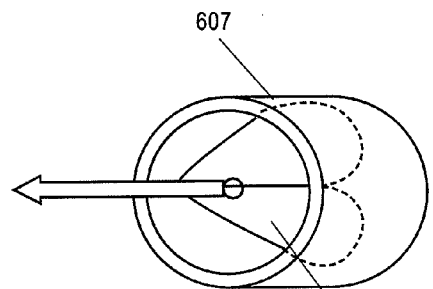

FIGS. 6A and 6B illustrate another variation of an airflow resistor. FIG. 6A is a perspective view of an airflow resistor including a hinged flap valve 601 during inhalation. An opening in the center of the hinged region 605 forms a leak pathway. The hinged flap valve is positioned within a passageway formed through a body region 607. During inhalation, the hinged flap opens, releasing the majority of the resistance and permitting air to flow around the hinged flap valve. During exhalation, shown in FIG. 6B, the flap valve closes occluding the passageway and increasing the resistance to expiration. An airflow resistor such as the one shown in FIGS. 6A and 6B may also be incorporated as part of a nasal device, similar to the variation shown in FIG. 5C.

Returning now to the airflow resistor shown in FIG. 4A, a flap valve layer 401 may include one or more flaps as part of the layer. Whole-nose nasal devices may have an elongated airflow resistor that may span the nasal region between the nostrils, as illustrated in FIGS. 2A-3B. In some variations the airflow resistor covers a portion or the entirety of both nostrils. Thus, it may be beneficial to have numerous flap valves formed within the flap valve layer. For example, the flap valve layer may have a plurality of flap valve leaflets cut or formed or attached to the flap valve layer. FIGS. 7A-8o illustrate different variations of flap valve layers that may be used. FIGS. 7A-7P show flap valve layers formed as rectangular-shaped layers. Each layer includes a plurality of valve leaflets cut into the airflow resistor layer. For example, in FIG. 7A, the leaflets are formed by cutting intersecting perpendicular lines at various points in the layer. Any of the layers shown may be positioned across from (or adjacent with) a flap valve limiting layer, allowing the flap valves to open substantially in only one direction.

FIG. 7N illustrates one other notable variation of a flexible flap valve. In this variation the elongate layer is formed in an oval shape, and the flap leaflets ("flaps") are cut into semi-circular or curved shapes resembling fish scales. FIGS. 8A-8o also show variations of flap valve layers in which the majority of the flaps are cut in curving, semi-circular ("fish scale") shapes. In FIGS. 8A-8o the overall perimeter of the flap valve layer (looking down on the major surface of the layer) has a curved figure "8" outer perimeter shape. In general, the flap valve layer may be surrounded by the holdfast layer, and thus, the perimeter of the flap valve layer may match the perimeter shape of the holdfast layer. Any flap valve layer may include one or more leak pathways, as shown in FIGS. 8a-8o (and also FIGS. 2B and 2C, above), although in some embodiments no separate leak pathway may be present in the flap valve layer. The orientation of the valve leaflets may be arranged in any desired fashion, some of which may provide advantages for controlling the resistance during expiration and inspiration. For example, multiple smaller flap valve leaflets (such as those shown in FIG. 8C, 8G, etc.) may have the advantage of opening reliably regardless of how the device is applied, since they may be less likely to interfere with adjacent skin when attached. Smaller valve leaflets may also be less noisy than larger flap leaflets when airflow passes through the nasal device.

A flap valve layer may be made of any appropriate material. For example, the flap valve layer may be made of polymeric materials, rubber (natural and synthetic), paper, fabric, or the like. Materials that may be used to form the flap valve layer include: latex, polyethylene, polypropylene, polystyrene, polyvinyl chloride, polyvinylidene chloride, polyvinyl acetate, polyacrylate, styrene-butadiene copolymer, chlorinated polyethylene, polyvinylidene fluoride, ethylene-vinyl acetate copolymer, ethylene-vinyl acetate-vinyl chloride-acrylate copolymer, ethylene-vinyl acetate-acrylate copolymer, ethylene-vinyl acetate-vinyl chloride copolymer, nylon, acrylonitrile-butadiene copolymer, polyacrylonitrile, polyvinyl chloride, polychloroprene, polybutadiene, thermoplastic polyimide, polyacetal, polyphenylene sulfide, polycarbonate, thermoplastic polyurethane, thermoplastic resins, thermosetting resins, natural rubbers, synthetic rubbers (such as a chloroprene rubber, styrene butadiene rubber, nitrile-butadiene rubber, and ethylene-propylene-diene terpolymer copolymer, silicone rubbers, fluoride rubbers, and acrylic rubbers), elastomers (such as a soft urethane, water-blown polyurethane), and thermosetting resins (such as a hard urethane, phenolic resins, and a melamine resins), and injection moldable materials such as polyether block amide (e.g., PEBAX®), and the like.

A flap valve layer may be made by cutting, molding, or otherwise forming a flap valve leaflet (or a plurality of flap valve leaflets) to from a layer of material having flap valve leaflets. In one variation, a layer of material (e.g., silicone, polyurethane, etc.) is die-cut to form the flap valve leaflets as part of a flap valve layer. Other methods of cutting may be used to form the valve or each valve leaflets, including laser cutting, jet cutting, or the like. In some variations, the flap valve is formed by molding. For example, the flap valve may be formed by thermoforming, injection molding, or the like. In some variations, the flap is made out of silicone or thermoplastic urethane. For example, the flap may be a thin and flexible piece of silicone. This flap may be any appropriate thickness that allows it to be flexible (e.g., to move from the open and closed positions). For example, the flap may comprise silicone that is between 0.0001 and 0.1 inches thick. In some embodiments, the silicone is approximately 0.002 inches thick. The flap valve layer may have variable thicknesses or comprise multiple layers, which may provide reinforcement or structural support for the valve layer.

Figure 9A:
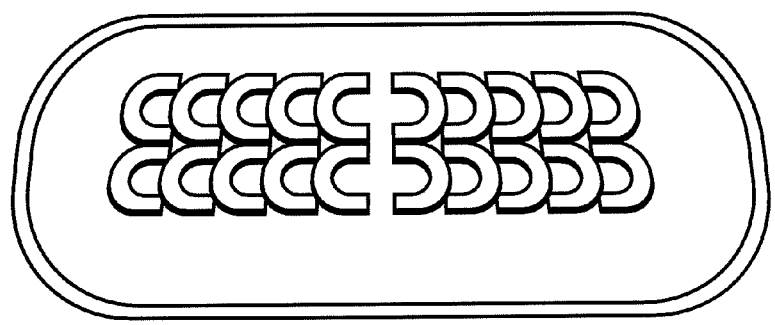
FIGS. 9A-9D are enlarged views of variations of flap valve layers of an airflow resistor.
Figure 9B:
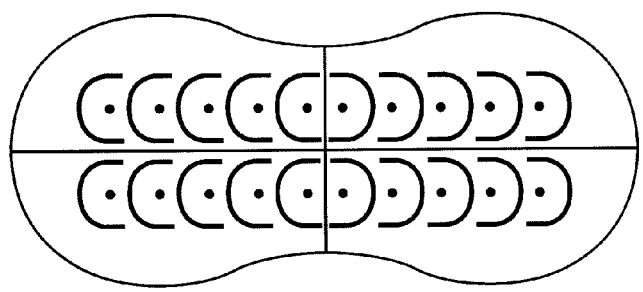
Figure 9C:
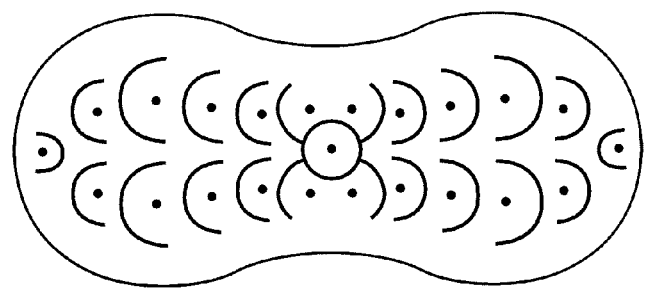

FIGS. 9A-9C are enlarged perspective views of three variations of flap valve layers that may be used, showing multiple flap valve leaflets arranged along the surface of the flap valve layer. As can be seen by comparing these various examples, flap valve leaflets can be different sizes, shapes and arrangements even on the same flap valve layer.

Figure 9D:
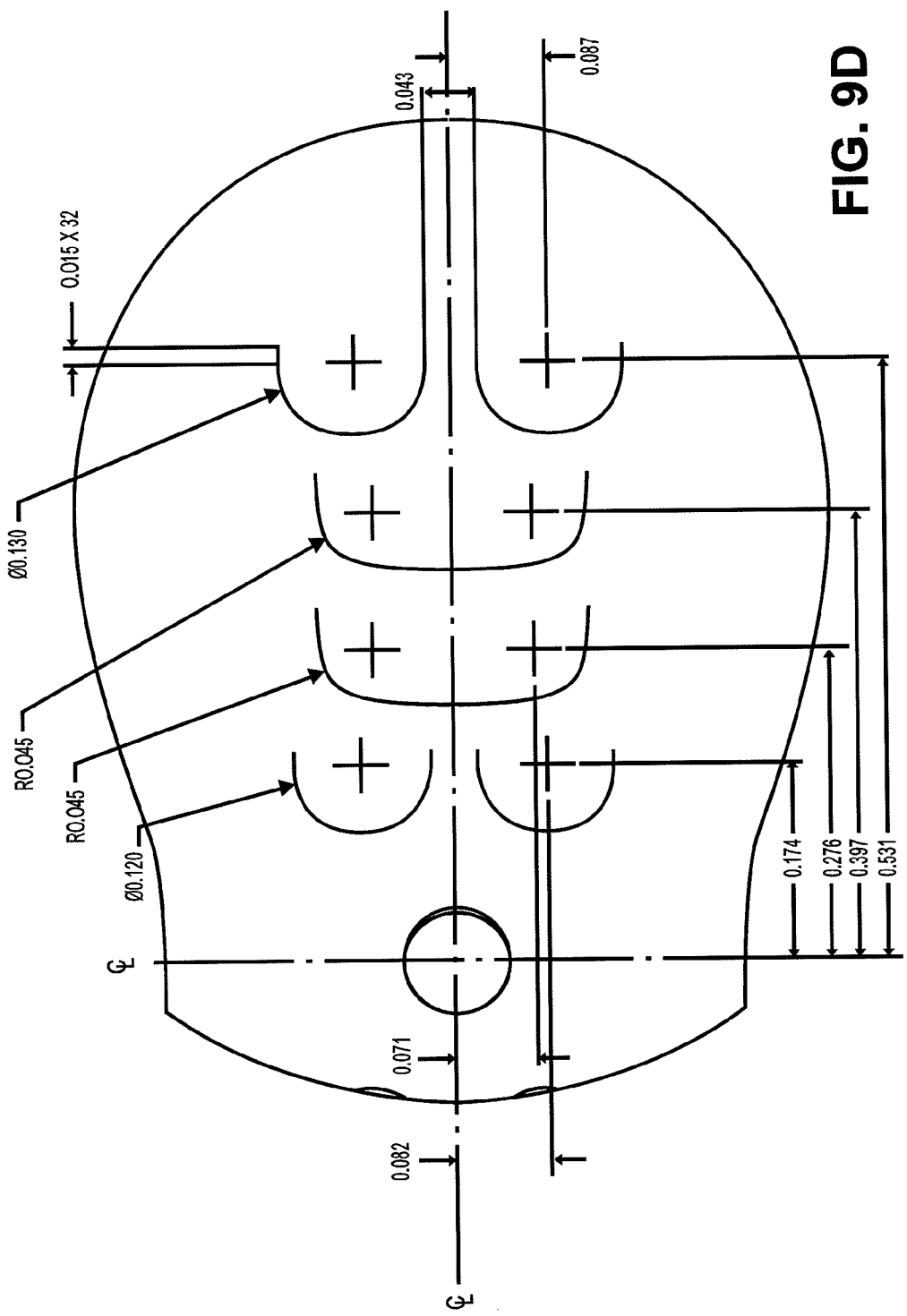

FIG. 9D is partial view of another variation of a flap valve layer. Overall, the layer has two "lobes" (and a generally figure-8 shaped perimeter). One lobe is shown in FIG. 9D, but (in this example) the opposite lobe is symmetrically arranged. Each lobe has six flap valves, including two larger central flap valves. In this example, the flap valves are spaced apart from each other, and from the edges of the flap valve layer, so that they can open and can close predictably (e.g., against an adjacent flap valve liming layer, not shown) when the device is worn in communication with the subject's nose. For example, this variation of the device includes flap valves that are separated from the perimeter of the flap valve layer by approximately the width of the valve opening, and each valve is separated from other valves by approximately 0.004 inches. Functionally, each valve is separated so that when the device is bent or curved to fit over the subject's nose, adjacent valves, and the portion of the flap valve layer immediately adjacent to the valve, does not block the flap from closing against the valve limiter layer during exhalation. If the area between valves in the flap valve layer is very thin (e.g., the spacing between valves is close), the strips of flap valve layer may bend or buckle when the device is applied to the subject's nose and prevent one or more of the flap valves from closing against the valve liming layer, resulting in a leak pathway around the flap valve. This may decrease the resistance to expiration in an unwanted (and difficult to predict) manner. Thus, the spacing between adjacent valves, and/or the arrangement of valves may be controlled to prevent this interference with the flap valve when the substantially flat device is applied to a subject's (non-flat) nasal region.

In some variations the flap valve layer and the adjacent valve limiting layer are adhered together so that the non-flap portions of the flap valve layer adhere to the valve limiting layer.

FIG. 9E is an exploded perspective view of the airflow resistor region of a whole-nose nasal devices. In this variation, the flap valve layer 919 is secured to the flap valve limiting layer 923 by an island of double-sided adhesive 921 that is placed between the layers. This double-sided adhesive layer extends around the perimeter, and also extends around the central leak pathway 909 formed through both the flap valve layer 919 and the valve limiting layer 923. In general, the valve limiting layer may include an opening for the leak pathway, as shown here. Although the valve limiting layer may be formed of a mesh or other air permeable material, cutting a leak pathway from the valve liming layer may enhance the predictability of the leak, and therefore the resistance to exhalation. Adhesively securing the region around the leak pathway formed in the flap valve layer and the valve limiting layer may help keep these openings in register, and may therefore help to regulate the size of the leak pathway opening and thus the expiratory resistance. The addition of double-sided adhesive may also help "stiffen" the leak pathway, preventing it from bucking or changing shape when the device is applied to the subject's nose. In some variations, an additional stiffening or support member may be added around the leak pathway.

The second island of double-sided adhesive 917 shown in FIG. 19E may help secure the airflow resistor assembly (consisting of the flap valve layer 919, the double-sided adhesive 921, and the valve limiting layer 923) to the rest of the nasal device, including the holdfast, as illustrated in greater detail in the examples below.

Adhesive Holdfast

The whole-nose nasal devices described herein may typically include an adhesive holdfast for securing the device to the subject. The adhesive holdfast may include one or more adhesive surfaces that are suitable for use against a subject's body (e.g., skin and/or nasal cavity). Thus, the adhesive holdfast may include a biocompatible adhesive. The adhesive holdfast may facilitate the positioning and securing of the device in a desired location with respect to the subject's nose. An adhesive holdfast may be configured to secure the device to any appropriate region of the subject's nose, nasal passage, or nasal cavity. Typically the whole-nose nasal device is secured around both of the subject's nostrils.

In general, the adhesive holdfast is configured to be applied predominantly to the outside of the nose (e.g., the skin). In some versions, the holdfast may also form a seal between the respiratory device and the nose, so air exchanged between the outside of the patient and the nostril must pass through the respiratory device. In some versions, the holdfast seals the device in communication with the nose completely, so that all air through the nostril (or nostrils) must be exchanged through the device. In some versions, the holdfast seal is incomplete, so that only some of the air exchanged between the patient and the external environment passes through the device. As used herein, "air" may be air from environment external to the patient, or it may be any respiratory gas (e.g., pure or mixed oxygen, $CO_2$, heliox, or other gas mixtures provided to the user).

The adhesive holdfast may be flexible so that it conforms to the surface of the subject's skin, which may be relatively irregularly shaped, and may include hair and the like. In some variations, the adhesive holdfast is made of a material that permits the passage of water vapor, liquid water, sweat and/or oil, which may enhance comfort. The adhesive holdfast may also include a texture or patterned relief surface to enhance bonding to the subject's nose region.

The adhesive holdfast may be made of layers. Thus, the adhesive holdfast may be referred to as a layered holdfast (or layered adhesive holdfast) For example, the adhesive holdfast may include a substrate layer to which a biocompatible adhesive is applied. The substrate is typically a flat (predominantly 2-sided) material that is flexible. An adhesive may be present on at least one surface of the substrate, allowing it to adhere to the subject's nasal region. In some variations, the substrate layer is itself adhesive without needing an additional adhesive. An additional protective cover may also be removably attached to the adhesive of the adhesive layer. The protective cover may allow the device (and particularly the adhesive holdfast) to be manipulated without inadvertently sticking the device to the fingers or other parts of the body and it may also prevent contamination of the adhesive. The liner may be a removable paper or other film that can be peeled off or otherwise removed to expose the adhesive. In some variations, the adhesive of the adhesive holdfast is activatable. For example, the adhesive becomes 'sticky' only after exposure to an activator (e.g., water, air, light, etc.). In some variations, an adhesive could be applied to the nose in a liquid form first, than the device is applied.

In some variations, a protective cover is not used. As already mentioned, in some variations, the substrate and adhesive are a single layer, so that the substrate comprises an adhesive material, or a material that can be activated to become adhesive. The adhesive holdfast may comprise any appropriate material. For example, the adhesive substrate may be a biocompatible material such as silicone, polyethylene, or polyethylene foam. Other appropriate biocompatible materials may include some of the materials previously described, such as biocompatible polymers and/or elastomers. Suitable biocompatible polymers may include materials such as: a homopolymer and copolymers of vinyl acetate (such as ethylene vinyl acetate copolymer and polyvinylchloride copolymers), a homopolymer and copolymers of acrylates (such as polypropylene, polymethylmethacrylate, polyethylmethacrylate, polymethacrylate, ethylene glycol dimethacrylate, ethylene dimethacrylate and hydroxymethyl methacrylate, and the like), polyvinylpyrrolidone, 2-pyrrolidone, polyacrylonitrile butadiene, polyamides, fluoropolymers (such as polytetrafluoroethylene and polyvinyl fluoride), a homopolymer and copolymers of styrene acrylonitrile, cellulose acetate, a homopolymer and copolymers of acrylonitrile butadiene styrene, polymethylpentene, polysulfones polyimides, polyisobutylene, polymethylstyrene and other similar compounds known to those skilled in the art. Structurally, the substrate may be a film, foil, woven, non-woven, foam, or tissue material (e.g., poluelofin non-woven materials, polyurethane woven materials, polyethylene foams, polyurethane foams, polyurethane film, etc.).

In variations in which an adhesive is applied to the substrate, the adhesive may comprise a medical grade adhesive such as a hydrocolloid or an acrylic. Medical grade adhesives may include foamed adhesives, acrylic co-polymer adhesives, porous acrylics, synthetic rubber-based adhesives, silicone adhesive formulations (e.g., silicone gel adhesive), and absorbent hydrocolloids and hydrogels.

In some variations, the adhesive is a structural adhesive. For example, the adhesive may adhere based on van der Walls forces. U.S. Pat. No. 7,011,723, U.S. Pat. No. 6,872,439, U.S. Pat. No. 6,737,160, and U.S. Pat. No. 7,175,723 describe structures whose shape and dimension provide adhesive force. These patents are herein incorporated by reference in their entirety.

Figures 10A, 10B, 10C:
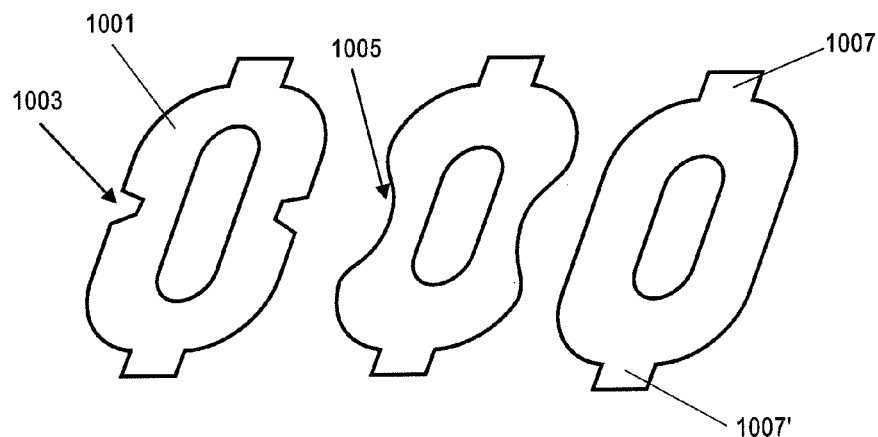
FIGS. 10A-10C illustrate variations of adhesive holdfasts.

FIGS. 10A-10C illustrate variations of the holdfast layers that may be used to form whole-nose nasal devices. In general, the holdfast layer or holdfast region is configured to surround the airflow resistor region, and to extend over both of a subject's nasal openings so that the nasal openings can be placed in communication with the airflow resistor. Thus, an adhesive holdfast may have an elongate shape both long and wide enough to extend at least partly or completely over and around the nasal openings. In general, the holdfast is longer than it is wide, and may include a curvature, slit, cut-out, or other region at the perimeter near the nasal region. The holdfast region may also include an opening that is somewhat centrally located so that both nostrils can communicate with the airflow resistor.

The whole-nose nasal devices described herein typically do not separate the airflow from the nostrils, but instead allow airflow from both nostrils communicate with a single airflow resistor (although multiple airflow resistors may be used). Thus, the holdfast region may include only a single opening for the airflow resistor.

Figure 11:
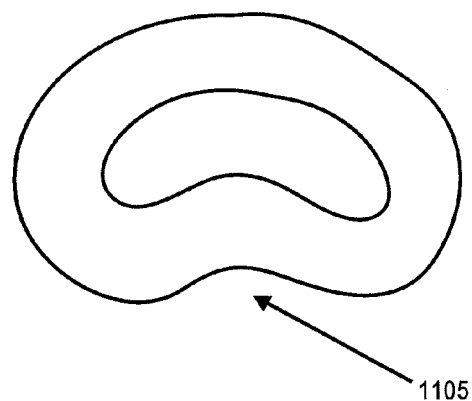
FIG. 11 is another variation of an adhesive holdfast.

For example, FIG. 10A shows a first variation of a holdfast region 1001 having a cut-out area 1003 along the perimeter near the midline of the long axis. This cut-out region may help the device conform to a subject's outer nose region. Other examples, such as those shown in FIGS. 10B and 11, include a curved (concave) region 1005, 1105 in the outer parameter of the adhesive holdfast, which may also help the device conform to the nose region (e.g., apron of the upper lip, nose tip region, and outer alar region. In some variations, the holdfast region is an elongate oval shape, as illustrated in FIG. 10C.

The holdfast region may also include one or more tabs or grips that may help a subject apply the device. For example, FIGS. 10A-10C all include tabs 1007, 1007' at either end of the device. Tabs and/or grips may be formed as part of the holdfast, or they may be separate and attached (or removable).

In general, the adhesive holdfast may comprise any appropriate shape that allows the airflow resistor to be positioned with respect to one or both nasal passages so that some (or most) of the airflow through the nasal passages must pass through the adhesive nasal device. In some variations, the adhesive holdfast attaches to the nose (or nasal passage) and forms a partial or complete seal therewith, thereby channeling airflow into or out of the nasal passageway through the device, and also securing the device in position.

It is not necessary that the entire adhesive holdfast region include an adhesive, although many of the substantially flat holdfast regions described in the preceding figures may have a biocompatible adhesive over much of the skin-contacting surface (which may be covered by a protective cover that can be at least partially removed later). In some variations only a subset of the holdfast region (including the outer layer) includes an adhesive. For example, a peripheral region may be adhesive-free (or may have had the adhesive weakened or removed), to help with applying/removing the devices (i.e., the region beneath any tabs or grips may not include an adhesive).

In some variations, the adhesive nasal devices described herein are adapted to fit different users having a diversity of sizes and shapes, particularly the shapes and sizes of their noses. As already described, the devices, including particularly the adhesive holdfast region, may be configured so that it is adaptable to different nose shapes. For example, the holdfast region may be flexible. In some variations, the holdfast region may extend into a nostril, rather than just adhering around it. For example, the adhesive holdfast may include a region that projects into the nostril, and can be secured at least partly against the walls of the nostril. In some variations, the internally-projecting regions may comprise a compressible material (e.g., a foam or the like) so that they may be secured within the nasal passages. In some variations, the inwardly-projecting portion (e.g., a guide or alignment region) of the nasal device may be smaller than the nasal opening, and does not necessarily contact the sides of the subject's nasal passage.

As mentioned above, any of the whole-nose nasal devices described herein may also include one or more removable liners. For example, a removable liner may cover the adhesive until the device is ready to be applied. A removable liner may be a removable liner layer. The removable liner may be made of any appropriate material that may be released from the adhesive. For example, the liner material may comprise Kraft paper. In some variations, the liner material comprises polyethylene film, or polyethylene coated paper (e.g. Kraft paper). The liner may be any of the other materials described herein.

In general, any of the materials commonly used in the manufacture of bandages (particularly disposable bandages such as Band-Aids™), ostomy kits, and wound care products may be used in any or all components of devices described herein. An adhesive layer (or an adhesive holdfast layer) may be formed in any appropriate method, particularly those described herein. For example, an adhesive layer may be formed by cutting (stamping, die cutting, laser cutting, etc.) the adhesive substrate, biocompatible adhesive, and protective cover into the desired shape. Multiple steps may be used to form the adhesive layer. For example, the adhesive layer may be formed by cutting (or otherwise forming) the outer perimeter, then by cutting (or otherwise forming) an inner opening.

EXAMPLES

Figure 12:
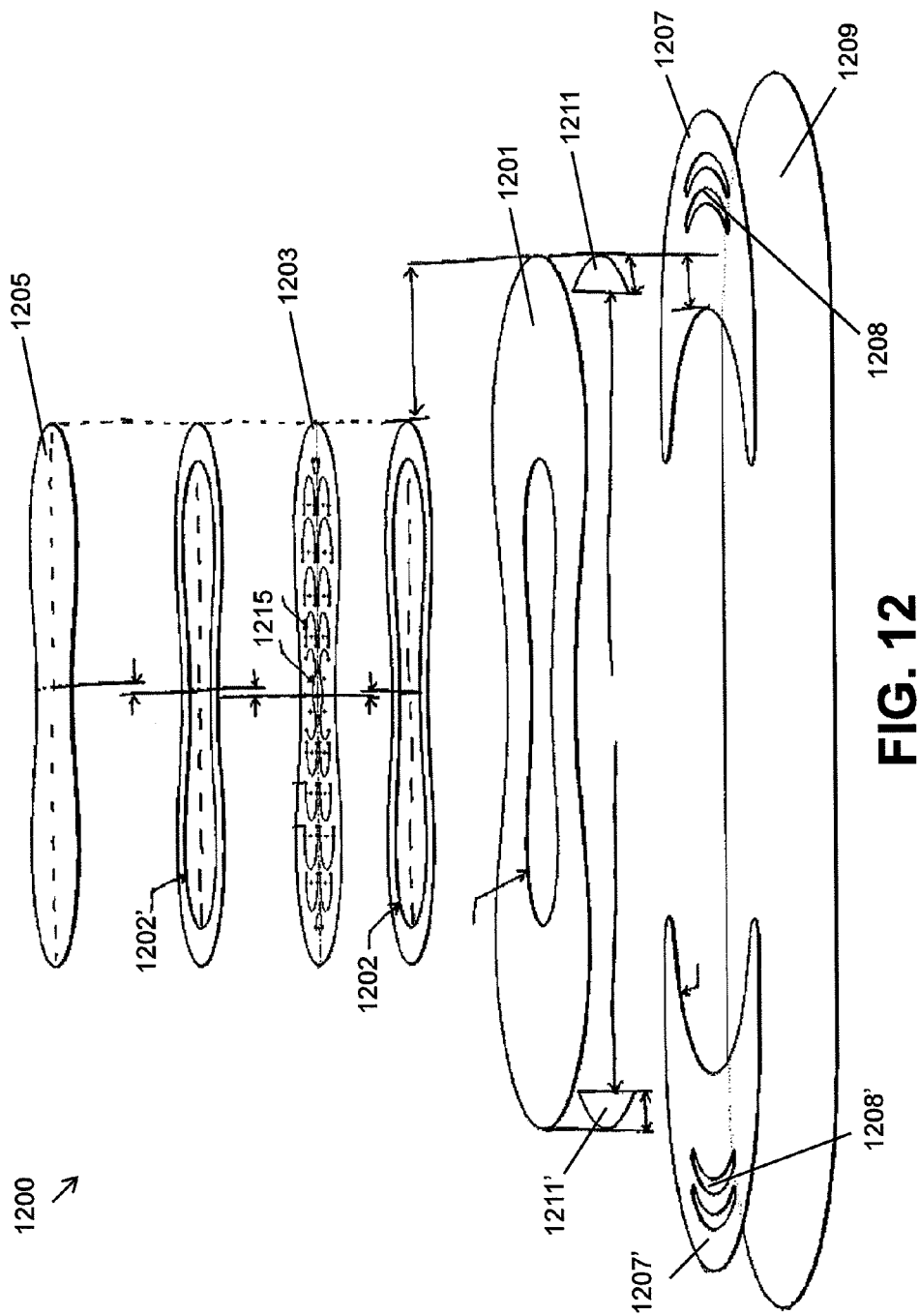
FIG. 12 is an exploded view of one variation of a whole-nose nasal device.
Figure 13:
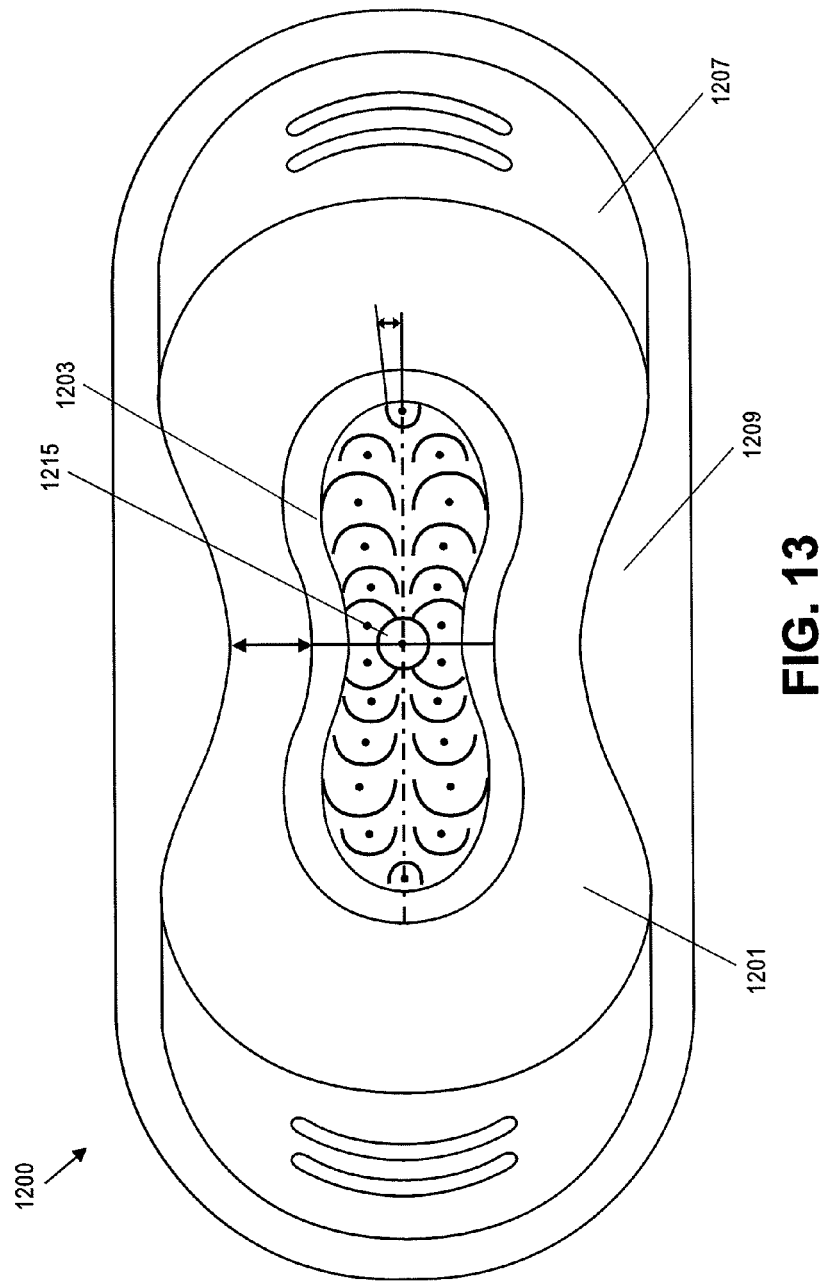
FIG. 13 is a view of the (assembled) device of FIG. 12, showing the side of the device configured to adhesively contact a subject.

FIG. 12 illustrates an exploded view of one variation of a whole-nose nasal device. This variation of a whole-nose nasal device is formed of layers, as illustrated. FIG. 13 shows a back view of the same whole-nose nasal device in the assembled form. In FIG. 12, the holdfast layer 1201 includes a biocompatible adhesive. The holdfast has a curved outer perimeter, and includes a central opening into which the airflow resistor (assembled from a flap valve layer 1203 and a flap valve limiter layer 1205) is positioned. A ring of adhesive 1202 (e.g., double-sided adhesive) is placed between the holdfast layer 1201 and the flap valve layer 1203. A second ring of adhesive 1202' is positioned between the flap valve layer 1203 and the flap valve limiter layer 1205, holding the two adjacent to each other and within the opening in the adhesive holdfast 1201.

Figure 18A:
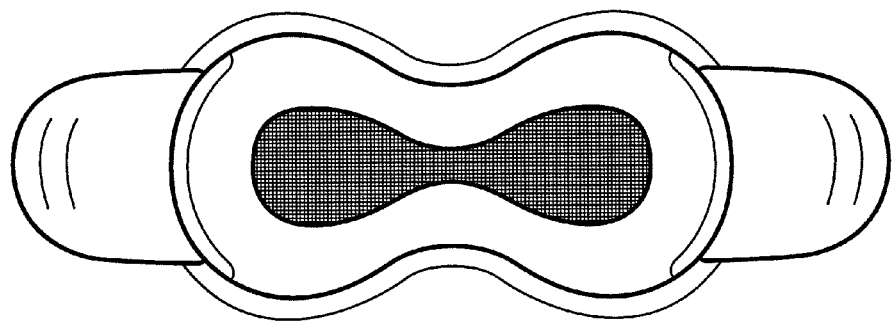
FIG. 18A-18C show variations of whole-nose nasal devices including grips or tabs.
Figure 18B:
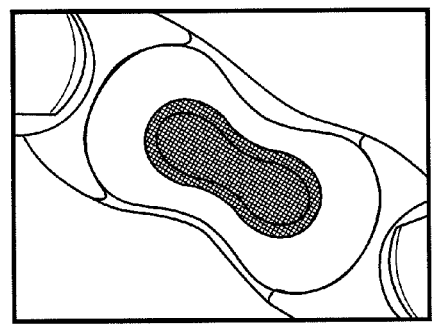
Figure 18C:
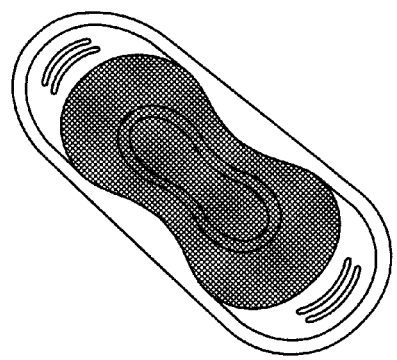

The example shown in FIGS. 12 and 13 also includes two removable grips or tabs 1207, 1207' that may be used to hold the device after removing it from a protective backing or covering layer 1209. For example, the protective backing may be peeled off to expose the adhesive shortly before applying the device. The grips or tabs 1207, 1207' may include textured, cut-out, or other grip regions 1208, 1208' to help identify or hold them. After removing the protective cover, a subject may hold onto the grip region(s) 1207, 1207' and apply the device to the nose. Once the device is positioned on the nose, the grips or tabs 1207, 1207' may be removed by pulling them off of the adhesive holdfast 1207. FIGS. 18A to 18C illustrate another variation of a whole-nose nasal device. In FIG. 18A, the whole-nose nasal device includes two grip regions, as described above in FIGS. 12 and 13, which may be removed during (or after) application of the device.

The whole-nose nasal device shown in FIGS. 12 and 13 also includes a central leak pathway 1215, which is an opening through the airflow resistor, as described above.

Figure 14A:
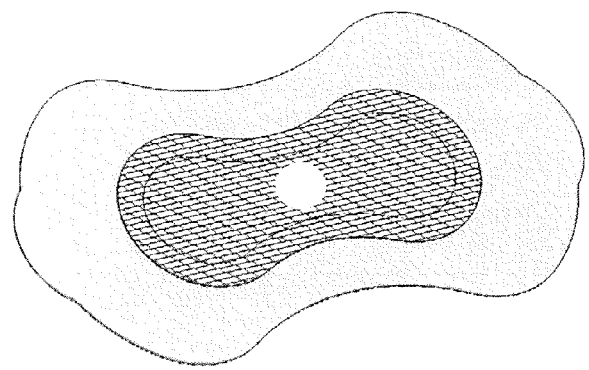
FIGS. 14A and 14B are perspective views of two variations of adhesive nasal devices.
Figure 14B:
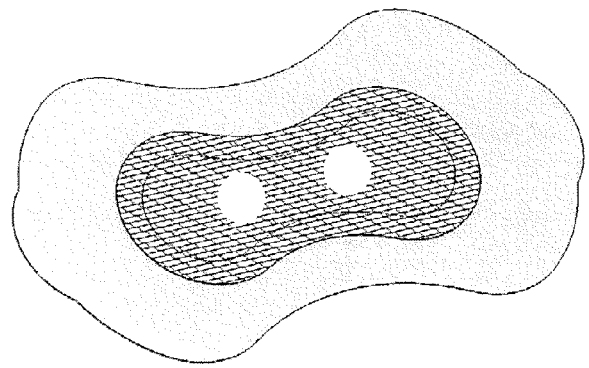

In the example shown in FIGS. 12 and 13, two peripheral regions of the adhesive holdfast also include non-adhesive regions 1211, 1211' that may help the subject remove the device after it has been used. The adhesive may either be uncoated, removed, or otherwise blocked (e.g., by attaching a piece of material (e.g., paper, fabric, etc.). As mentioned, FIG. 13 illustrates the assembled whole-nose nasal device attached to a protective layer. Similarly, FIGS. 14A and 14B illustrate perspective front views of whole-nose nasal devices.

Figure 15:
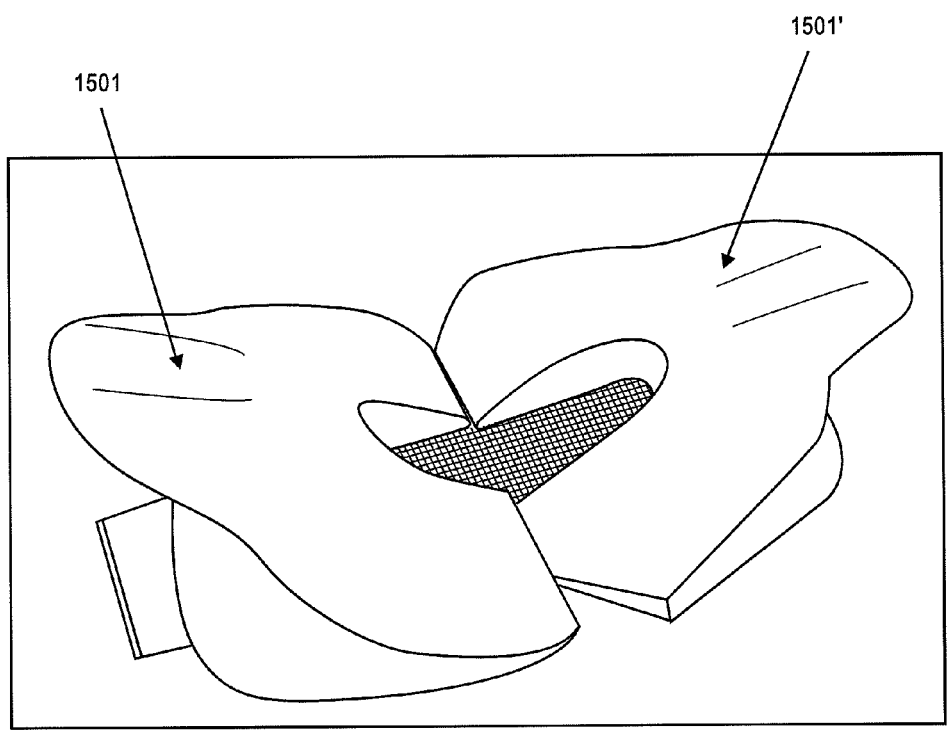
FIG. 15 is a perspective view of another variation of a whole-nose nasal device including a protective cover.
Figure 16A:
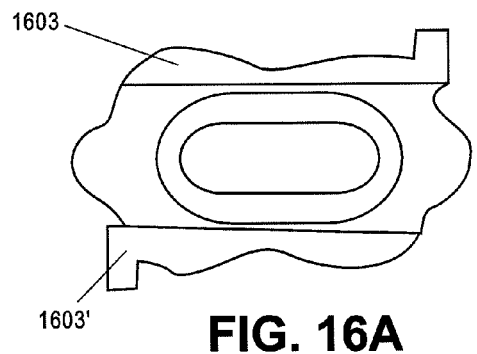
FIGS. 16A-16D show whole-nose devices including support frames.
Figure 16B:
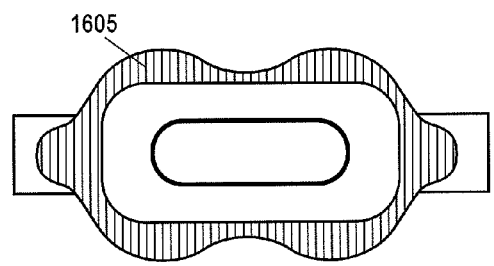
Figure 16C:
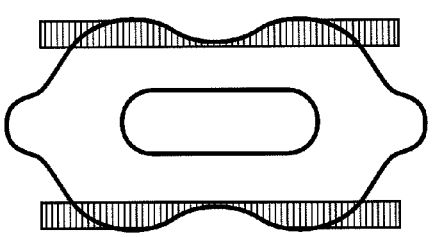

In some variations the protective backing or protective layer may be used as a tab or grip that can help position the device on the subject's nose. For example, FIG. 15 shows one variation of a device having two protective layers 1501, 1501' that cover at least a portion of the nasal device. This protective layer protects the adhesive, but can be removed by pulling either (or both) tabs to expose the adhesive. The backing layer may also help apply the device by supporting or preventing the otherwise flexible holdfast layer from folding back on itself. In some variations the holdfast layer is extremely flexible, and may be difficult to handle. FIGS. 16A-C illustrate another variation of a whole-nose nasal device having a support structure, frame or stiffener for helping maintain the shape of the holdfast or preventing it from sticking to itself or to the subject's fingers or other undesirable targets.

Figure 16D:
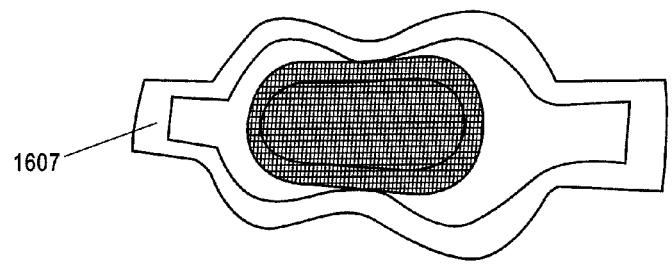

FIG. 16A illustrates a variation of a whole-nose nasal device having two frame regions 1603, 1603' that are formed of a stiff material to prevent the edges of the device from wrinkling or sticking together. In FIG. 16A the two parallel frame regions 1603, 1603' are removable once the device has been applied, or immediately before applying the device. In FIG. 16B, a frame region 1605 at least partially surrounds the adhesive holdfast. In some variations the frame region 1605 is removable. In other variations, the frame region 1605 is not removable, or is intended to remain on the subject with the rest of the device. Thus, the frame may be flexible as well, but generally has a greater stiffness than the holdfast region alone. FIG. 16C is similar to the variation shown in FIG. 16A, and FIG. 16D is similar to the example of FIG. 16B. The frame 1607 of FIG. 16D may be removed or left on when worn, as illustrated in FIG. 17.

Figure 17:
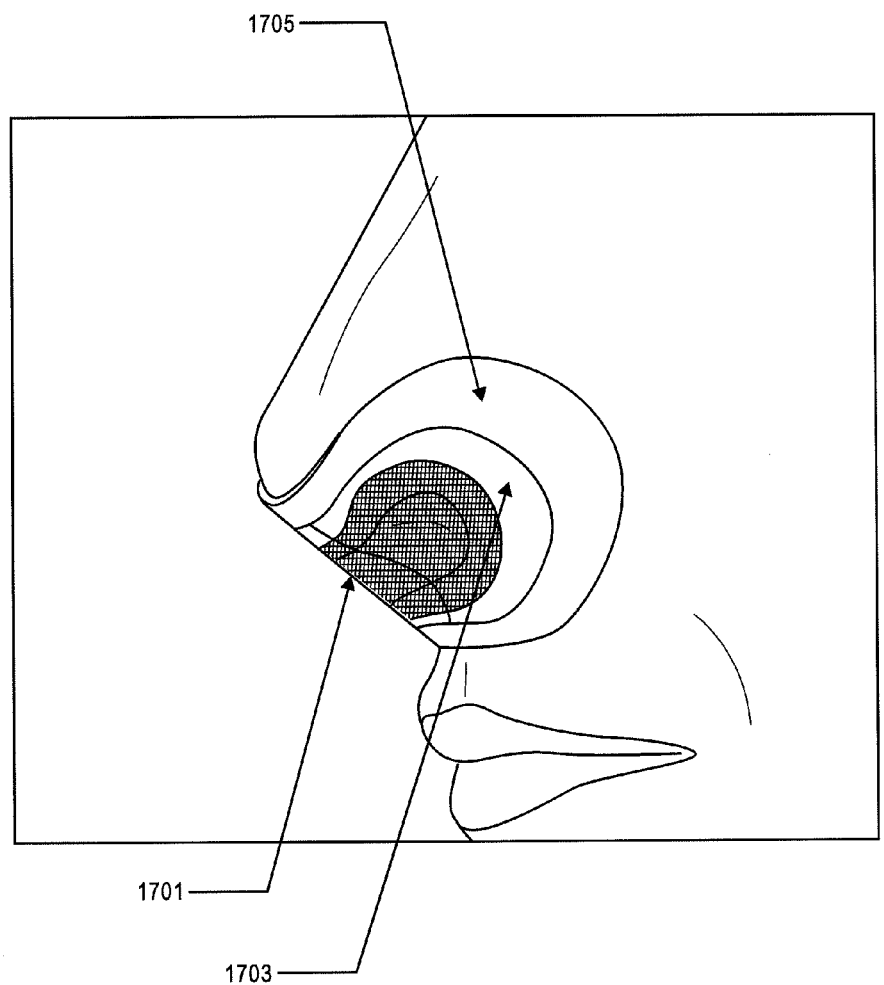
FIG. 17 shows a subject wearing a whole-nose nasal device including a support frame.

In FIG. 17 a whole-nose nasal device is applied to the subject's nose so that both nostrils communicate with the airflow resistor 1701 (formed by an adjacent flap valve layer and a flap valve limiter layer). A frame 1705 surrounds the perimeter of the adhesive holdfast 1703 (in this example the adhesive holdfast is formed of 2 mil polyurethane and a biocompatible adhesive). The frame may include an adhesive and directly adhere to the skin itself, or it may be applied on the outside (the distal side) of the adhesive holdfast, so that the frame does not contact the skin.

FIGS. 19A to 24B illustrate another variation of a whole-nose nasal device in detail. FIG. 19A is a front view of one variation of a whole-nose nasal device, and FIG. 19C is a perspective view of the same nasal device. An exploded view is provided in FIG. 19B, indicating that this device may include six layers, including the protective cover or backing 1913. For example, the adhesive holdfast layer 1901 is connected to the airflow resistor, which is formed from the flap valve layer 1903 and the flap valve limiter layer 1905. Two adhesive layers 1902, 1902' are included to secure these different layers together (see also FIG. 9E, 917, 921). A non-adhesive tab 1909 may also be included. Each of these layers is illustrated in greater detail in FIGS. 20A-24B.

Figures 20A, 20B:
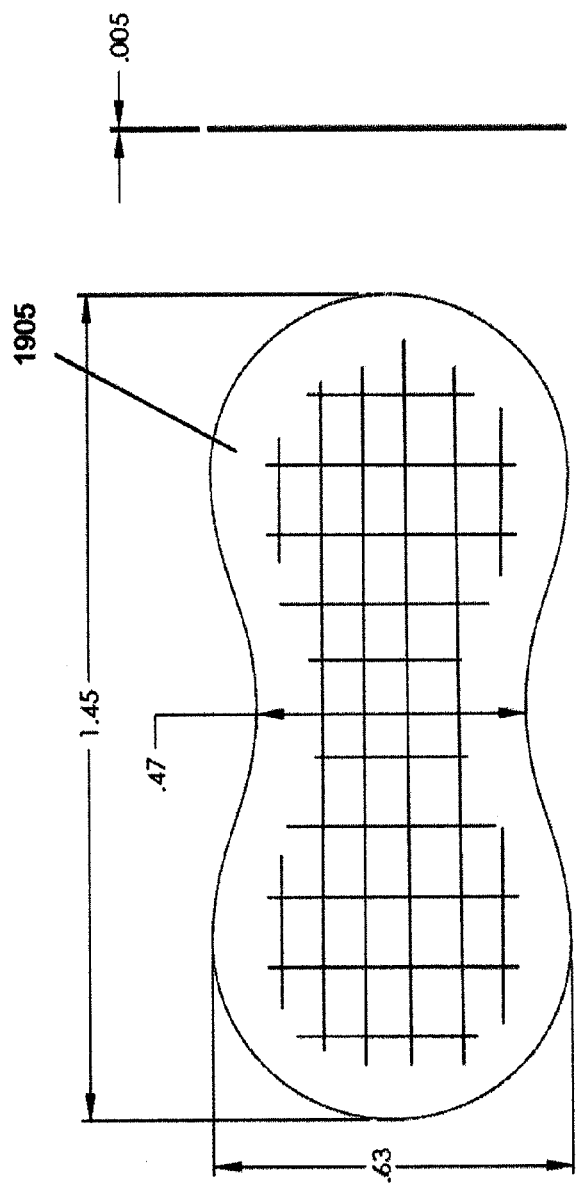
FIG. 20A is an enlarged view of the flap valve limiter layer of the device of FIGS. 19A-19C.
FIG. 20B is a side view of the flap valve limiter of FIG. 20A. The dimensions shown are merely examples of dimensions that may be appropriate.

For example, the outermost layer of the airflow resistor is the flap valve limiter layer 1905, an example of which is shown in FIG. 20A and 20B. Exemplary dimensions are provided in all of FIGS. 19A-24B, and are intended only to illustrate one possible variation. Other dimension, including other shapes and arrangements in keeping with this disclosure, are also intended to be included. In FIG. 20A, the flap valve limiter layer 1905 is an airflow-permissive layer such as a mesh or grid of material. Typically this flap valve limiter layer includes relatively large openings which do not act as a 'filter' (e.g., capable of filtering small particles such as dust), although a filter material may be used as a flap valve limiter in some variations. FIG. 20B shows a side view of the flap valve limiter layer 1905, indicating that it is a thin layer. In this example, the flap valve limiter layer is also flexible.

FIGS. 21A-21C illustrate one variation of an adhesive holdfast layer 1901. FIG. 21A shows a front view of the non-adhesive side of the holdfast layer. FIG. 21B shows a side view of the holdfast layer. FIG. 21C shows a back view of the adhesive side of the holdfast layer. In this example, the adhesive holdfast includes a cutout or center opening 1921 into which the airflow resistor fits. Two peripheral edge regions 1923, 1923' are not adhesive. For example, adhesive may be selectively applied to the entire back surface except for these regions, or these regions may be de-tacked by covering with a material (e.g., polyurethane strip).

Figure 22A:
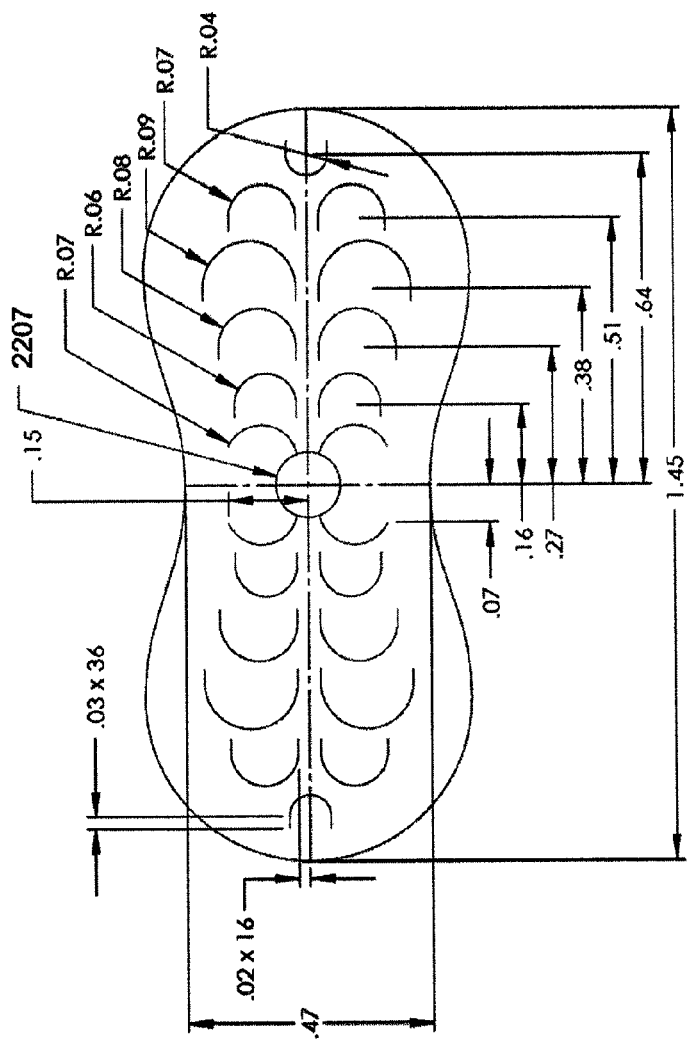
FIGS. 22A and 22B are front and side views respectively of a flap valve layer forming part of the device shown in FIGS. 19A-19C. The dimensions shown are merely examples of dimensions that may be appropriate.
Figure 22B:
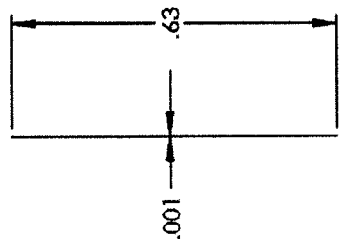

FIGS. 22A and 22B show one variation of a flap valve layer from a front view and a side view, respectively. This variation of a flap valve layer include a plurality of "fish-scale" type flaps arranged across the surface of the airflow resistor layer. The layer is symmetric about the long axis center line. This device also includes a central opening (leak pathway 2207).

Figures 23A, 23B:
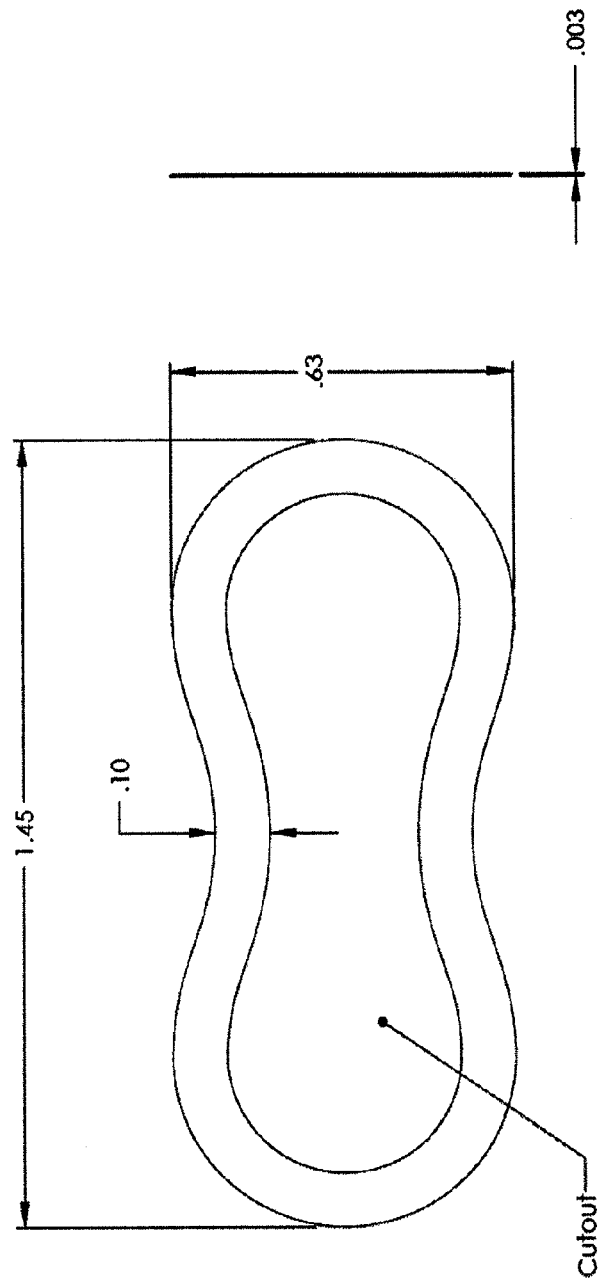
FIG. 23A is an enlarged view of an adhesive island forming part of the device of FIGS. 19A-19C.
FIG. 23B is a side view of the adhesive island. The dimensions shown are merely examples of dimensions that may be appropriate.

FIGS. 23A and 23B show an example of an adhesive "island" or layer that may be positioned between the holdfast and airflow resistor (e.g., flap valve layer or other region) and/or between the flap valve limiter layers to secure them together. FIG. 9E shows another example of adhesive islands. In some variations a separate "layer" is not used, but adhesive is painted, sprayed, stamped, coated, or otherwise applied to secure these layers together. In some variations methods such as heat-staking, melting, welding, etc. are used. In FIG. 23A and 23B the adhesive island is formed from a double-sided tape or adhesive material.

Figures 24A, 24B:
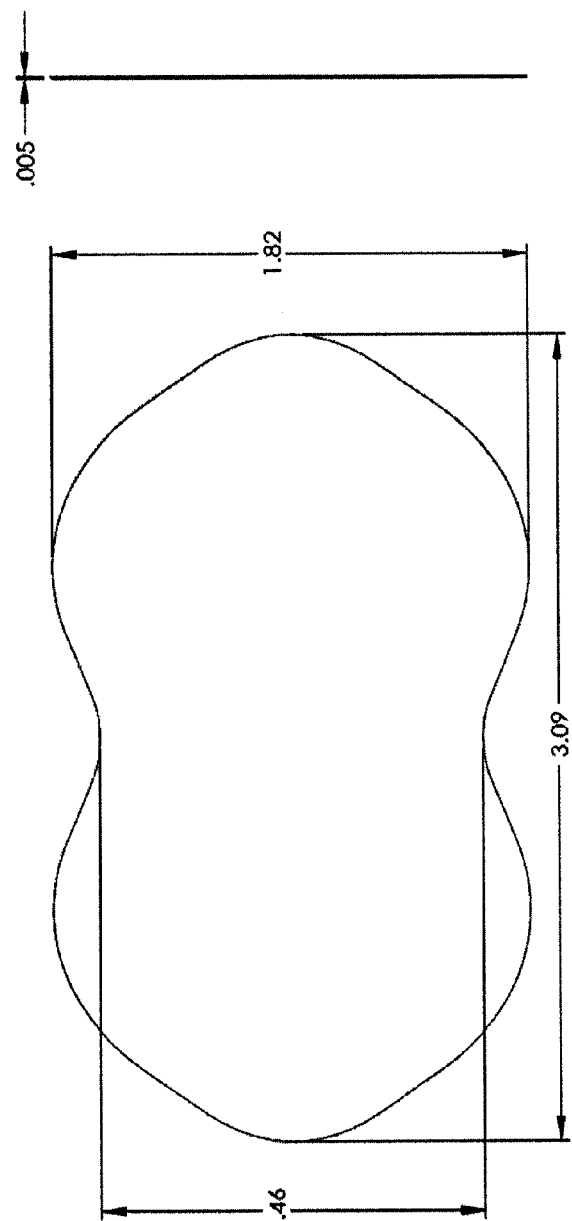
FIG. 24A is a front view of the liner portion of the device shown in FIGS. 19A-19C.
FIG. 24B is a side view of the liner shown in FIG. 24A. The dimensions shown are merely examples of dimensions that may be appropriate.

FIGS. 24A and 24B show one variation of a removable protective layer from the front and side, respectively. This layer may be referred to as a liner (or protective liner). A protective layer may allow the device (and particularly the adhesive holdfast) to be manipulated without inadvertently sticking the device to the fingers or other parts of the body and it may also prevent contamination of the adhesive. The liner may be a removable paper or other film that can be peeled off or otherwise removed to expose the adhesive. In some variations, a protective cover is not used.

Figure 25A:
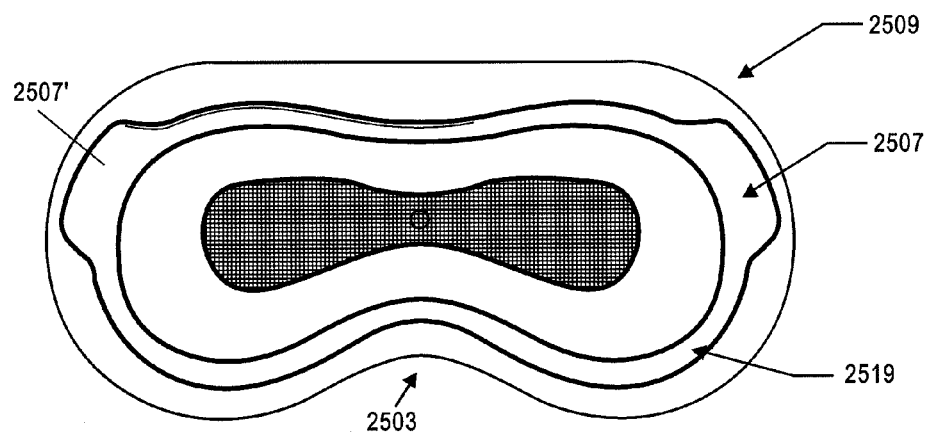
FIG. 25A and 25B show another example of a whole-nose nasal device both with (FIG. 25A) and without (FIG. 25B) a protective liner.
Figure 25B:
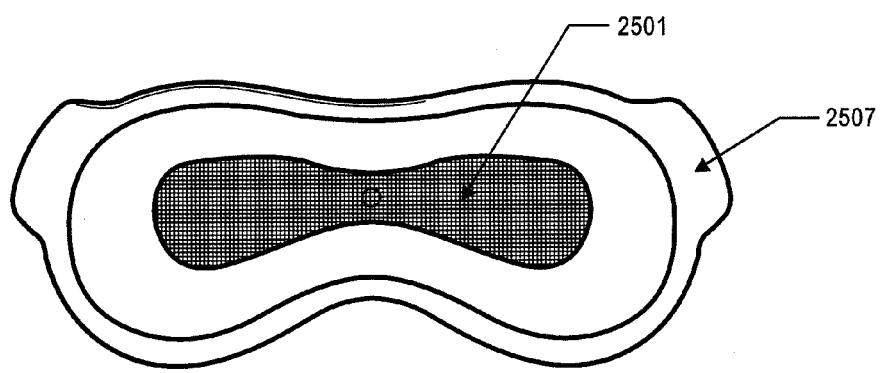

FIGS. 25A and 25B illustrate another variation of a nasal device as described herein. The nasal device shown in FIG. 25A includes an asymmetric liner 2509, which includes a curved perimeter on one side that may provide tactile feedback to the subject helping to orient how the device may best be applied. In this example, the entire nasal device is oriented so that the region of the greater inner curvature 2503 may fit under the middle of the nose, allowing the tabs 2507, 2507' to be placed over the sides (alar regions) of the nose. FIG. 25B shows the device of FIG. 25A without the protective liner layer 2509. In this example the tabs 2507, 2507' may be part of a frame. The frame may be part of the device that is left on the device when worn, or it may be removed after applying the device, as described above. For example, in FIG. 25A and 25B, the frame 2519 may be an integral part of the device.

Figure 25C:
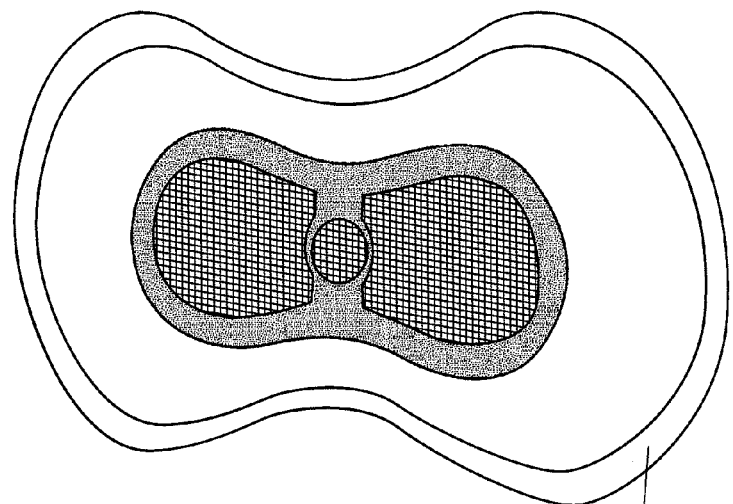
FIG. 25C and 25D show alternative examples of whole-nose nasal devices including a frame region supporting the outer edge.
Figure 25D:
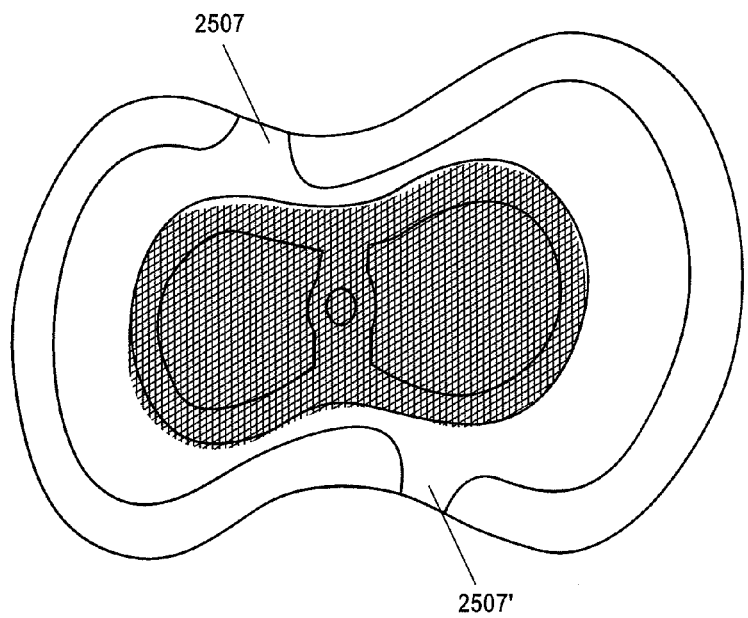

FIGS. 25C and 25D show two addition examples of whole-nose nasal devices. For example, in FIG. 25C a frame region 2519 along the outer edge of the device provides support and structure to the device. The other regions of the device are substantially as described above, including an adhesive holdfast, and a flexible airflow resistor having a plurality of flap valves ("fish scale" type flap valves) and a flap valve limiting layer. A central leak pathway is open during both exhalation and inhalation. In this example, the frame region 2519 is a thin urethane layer which provides an enhanced thickness to the nasal device. This frame is configured to remain on the nasal device when it is worn.

FIG. 25D illustrates another example of a whole-nose nasal device. In this example, the frame comprises two removable sections, 2507, 2507' that may be peeled off (or otherwise removed) after the device has been applied. For example, the frame may be an additional layer of liner (or protective backing) that may be peeled off. Forming the frame in two or more sections may make it easier to remove.

Methods of Use

In operation, the whole-nose nasal devices described herein may be applied to the subject's nose so that both nostrils are in communication with the airflow resistor. The airflow resistor can then modify the flow of air through the nose by increasing the resistance to exhalation more than the resistance to inhalation. As described above, these devices may be used to treat respiratory or related disorders such as sleep apneas, snoring, or the like. As a method of treating, the devices may be applied and adhesively secured so that the airflow resistor is in communication with airflow through both nostrils. The subject may then be allowed to breathe normally while wearing the device. Treatment may be during sleep (e.g., for snoring). In some variations, measurements of respiration, airflow, and/or sleep cycles may be performed while the subject is wearing the device, which may be useful to titrate or monitor treatment.

A subject may apply the device to his or her own nose. For example, a whole-nose device may be first removed from clean or sterile packaging. The devices described herein may be sized (e.g., child/adult, small, medium, large, etc.), or one-size-fits-all. Placement of a whole-nose nasal device may be done in front of a mirror or can be done without looking at a mirror. A device having an adhesive holdfast with a protective cover may be prepared for application by first removing the protective cover. The device may then be applied over the nostrils by gently pushing the adhesive holdfast against the nostril to secure the airflow resistor in communication with the nostrils. After placement of the nasal device, the user may test whether an adequate seal has been created or has been maintained between the adhesive holdfast and the nostrils through a variety of methods. On exhalation, for example, it may be clear to the user whether a good seal has been created between the device and his nasal cavity based on the feel. Alternatively, the user can use his finger to plug or occlude the leak pathway. If there is an adequate seal between the device and the user's skin while the leak pathway is occluded, expiration will be very prolonged. In general, the whole-nose device may be removed by peeling the adhesive holdfast away from the nostril. If a good seal has not been formed, the device may be removed and reapplied, or a new device may be applied.

Figure 26A:
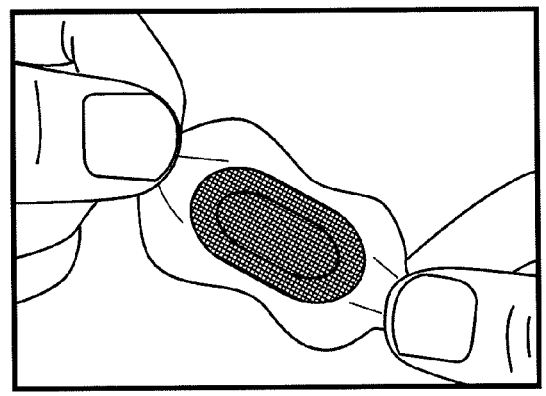
FIG. 26A illustrates application of a whole-nose nasal device to a subject's face.
Figure 26B:
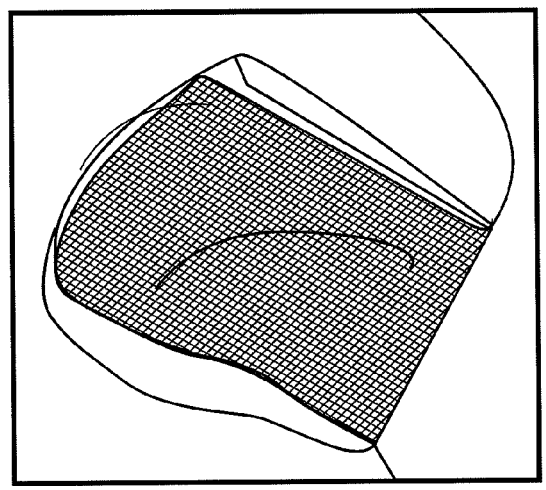
FIGS. 26B-26C illustrate adhesive nasal devices applied to a subject's nose.
Figure 26C:
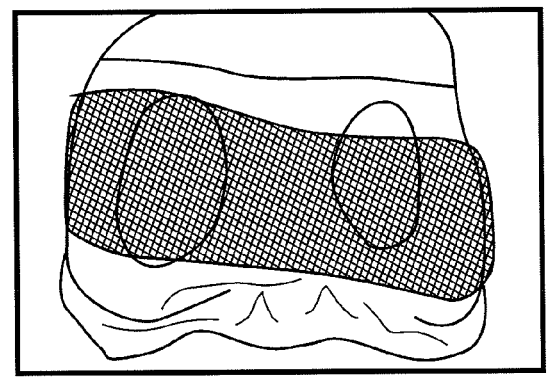

FIGS. 26A-26C illustrate one variation of applying a whole-nose nasal device. In FIG. 26A, the adhesive surface of the whole-nose nasal device is exposed by removing a protective layer, or by activating or applying an adhesive material to the back side of the holdfast layer. The device may be held by grasping tabs on either side. The back side (including the exposed adhesive) may then be applied to the subject's nose, as indicated in FIGS. 26B and 26C. The device is typically applied so that the airflow resistor portion, which is surrounded by the holdfast region, spans both of the subject's nostrils, as shown. Because the airflow resistor region is larger (e.g., extends further) than the typical distance of the nostril openings and the space between them, the alignment does not have to be precise. The device is oriented so that the flaps of the airflow resistor layer (in this example) open inward during inhalation and close during exhalation.

The flexible device generally covers the subject's nostrils by wrapping around the nose in the region over the nostrils, as shown. FIGS. 27A-27D show different illustrations of whole-nose nasal device applied to different subjects. In general, a subject may apply the whole-nose nasal device to themselves, and may apply gentle pressure to secure the device in position against the face or nose. A seal may form between the device and the area around the nostril openings, as mentioned above. The device may fit snugly against the subject's nose, and across the nasal opening. In some variations a spacer or aligner may be used to help position the device.

Figures 28A, 28B:
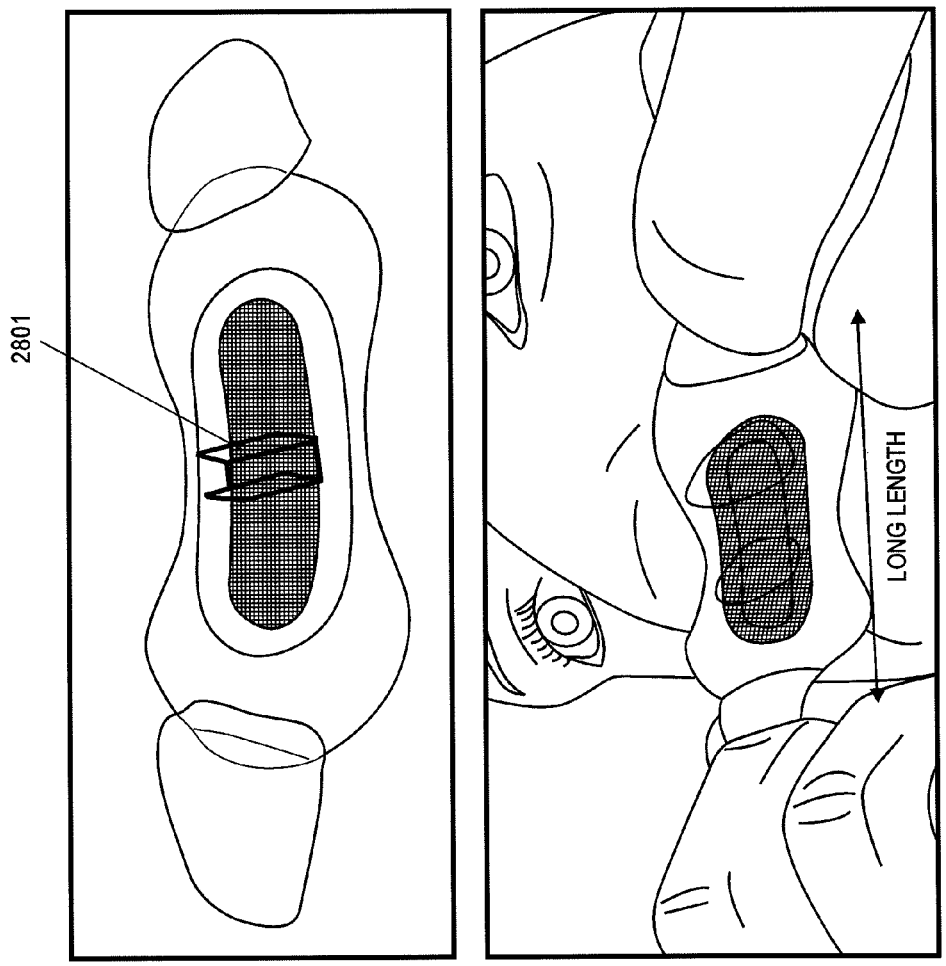
FIG. 28A is another variation of a whole-nose adhesive nasal device and FIG. 28B shows the application of the nasal device of FIG. 28A.

For example, FIG. 28A illustrates one variation of a whole-nose nasal device including a spacer 2801 that may be used to position the nasal device with respect to the subject's nose, as illustrated in FIG. 28B. For example, the spacer may be bridge or protrusion at or near the midline of the device. During application, the subject may use this spacer to center the device (along the long axis) with respect to the midline of the nose (i.e., the septal region).

In some variations the spacer may also maintain the device (e.g., the airflow resistor region of the device, or a portion of the airflow resistor) from the nasal openings. For example, a spacer may prop the device against the septal region of the nose, spacing the inner surface of the device (e.g., the flap valve layer) from the septum, nasal opening, or edge of the nostrils.

Any of the devices described herein may be fabricated using any appropriate technique, including continuous or batch manufacturing techniques. For example, FIG. 29A illustrates one variation of a continuous manufacturing technique. In this example, layers are applied and secured together, either all at once, or separately. Layers of substrate (adhesive holdfast 2901) may be applied to layers forming the airflow resistor (flap valve layer 2903 and flap valve limiter layer 2905). After assembling the layers, individual whole-nose devices may be cut out. FIG. 29B shows one variation of a device formed by such a continuous method. FIG. 29C shows a similar device formed in an alternative orientation.

While the methods and devices have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the invention.

What is claimed is:

1. A nasal respiratory device to be worn when sleeping, the device comprising:
    a flexible and substantially flat body configured to secure at least partially over both of a subject's nostrils, wherein the body includes a valve region and a holdfast region;
    wherein the valve region is configured to inhibit exhalation through the nostrils more than inhalation through the nostrils; and further
    wherein the holdfast region is configured to adhesively secure the device around a subject's nostrils.

2. The device of claim 1, wherein the valve region comprises a flap valve.

3. The device of claim 1, wherein the valve region comprises a plurality of flap valves.

4. The device of claim 1, further comprising an opening through the body that is open to allow airflow during both exhalation and inhalation.

5. The device of claim 1, further wherein the valve region comprises a flap valve layer adjacent to a flap valve limiter layer.

6. The device of claim 1, wherein the holdfast region surrounds the airflow resistor.

7. The device of claim 1, wherein the resistance to exhalation is between about 1 and about 250 cm $H_2O$/L/sec.

8. The device of claim 1, wherein the resistance to inhalation is between about 0.01 and about 5 cm $H_2O$/L/sec.

9. The device of claim 1, wherein the adhesive holdfast region comprises a substrate and a biocompatible adhesive.

10. The device of claim 1, wherein the body is substantially elongate.

11. The device of claim 1, wherein an outer perimeter of the body includes an inwardly curving region.

12. The device of claim 1, further comprising a removable protective cover layer covering at least part of the holdfast region.

* * * * *